(12) United States Patent
Gutierrez

(10) Patent No.: US 11,260,074 B2
(45) Date of Patent: *Mar. 1, 2022

(54) COMPOSITIONS AND RELATED METHODS FOR RECONSTITUTING THE IMMUNE SYSTEM OF A SUBJECT

(71) Applicant: Enrique G. Gutierrez, Saint Cloud, FL (US)

(72) Inventor: Enrique G. Gutierrez, Saint Cloud, FL (US)

(*) Notice: Subject to any disclaimer, the term of this patent is extended or adjusted under 35 U.S.C. 154(b) by 22 days.

This patent is subject to a terminal disclaimer.

(21) Appl. No.: 16/818,876

(22) Filed: Mar. 13, 2020

(65) Prior Publication Data

US 2020/0215105 A1 Jul. 9, 2020

Related U.S. Application Data

(63) Continuation-in-part of application No. 15/129,339, filed as application No. PCT/US2015/022513 on Mar. 25, 2015, now Pat. No. 10,624,923.

(60) Provisional application No. 61/967,804, filed on Mar. 26, 2014.

(51) Int. Cl.
  *A61K 33/24* (2019.01)
  *A61P 37/04* (2006.01)
  *A61K 45/06* (2006.01)
  *A61K 31/175* (2006.01)

(52) U.S. Cl.
  CPC .......... *A61K 33/24* (2013.01); *A61K 31/175* (2013.01); *A61K 45/06* (2013.01); *A61P 37/04* (2018.01)

(58) Field of Classification Search
  None
  See application file for complete search history.

(56) References Cited

U.S. PATENT DOCUMENTS

| | | | |
|---|---|---|---|
| 5,093,327 A | 3/1992 | Gomaille et al. | |
| 5,578,606 A | 11/1996 | Vazquez et al. | |
| 5,885,980 A | 3/1999 | Gutierrez et al. | |
| 10,624,923 B2 | 4/2020 | Gutierrez | |
| 2002/0013268 A1 | 1/2002 | Fryburg et al. | |
| 2005/0233946 A1 | 10/2005 | Fine et al. | |

FOREIGN PATENT DOCUMENTS

| | | |
|---|---|---|
| DE | 43 36 642 A1 | 4/1995 |
| WO | WO 88/00236 A1 | 1/1988 |
| WO | WO 02/24207 A1 | 3/2002 |
| WO | WO 2015/148684 A2 | 10/2015 |

OTHER PUBLICATIONS

Yarmohammadi et al. (Ann Allergy Asthma Immunol. Oct. 2017; 119(4): 374-378).*

Cusi, et al., "Vanadyl Sulfate Improves Hepatic and Muscle Insulin Sensitivity in Type 2 Diabetes," *Journal of Clinical Endocrinology & Metabolism*, 86(3):1410-1417, (2001).

Proks, et al., "Interaction of Vanadate with the Cloned Beta Cell $K_{ATP}$ Channel," *The Journal of Biological Chemistry*, 274(36):25393-25397, (1999).

Wong, et al., "Physiologically Stable Vanadium (IV) Porphyrins as a New Class of Anti-HIV Agents," *Chem. Commun.*, pp. 3544-3546, (2005).

Shigeta, et al., Antiviral Research 58 (2003) 265-271.

D'Cruz, et al., "Potent Dual Anti-HIV and Spermicidal Activities of Novel Oxovanadium(V) Complexes With Thiourea Non-Nucleoside Inhibitors of HIV-1 Reverse Transcriptase," *Biochemical and Biophysical Research Communications*, 302:253-264. (2003).

Rehder, "Vanadium. Its Role for Humans," *Metal Ions in Life Sciences*, 13:139-169, (2013).

Kabadi, et al., "Weight Gain, Improvements in Metabolic Profiles and Immunogenicity with Insulin or Sulphonylurea Administration in AIDS," *Clinical Drug Investigation*, 24(5):287-294, (2004).

Lederman, Michael M., et al. "Residual immune dysregulation syndrome in treated HIV infection." *Advances in immunology*. vol. 119. Academic Press, 2013. 51-83.

Jain, Vivek, et al. "Antiretroviral therapy initiated within 6 months of HIV infection is associated with lower T-cell activation and smaller HIV reservoir size." *The Journal of infectious diseases* 208.8 (2013): 1202-1211.

Ravimohan, Shruthi, et al. "Early immunologic failure is associated with early mortality among advanced HIV-infected adults initiating antiretroviral therapy with active tuberculosis." *The Journal of infectious diseases* 208.11 (2013): 1784-1793.

Lu, Wei, et al. "CD4: CD8 ratio as a frontier marker for clinical outcome, immune dysfunction and viral reservoir size in virologically suppressed HIV-positive patients." *Journal of the International AIDS Society* 18.1 (2015): 20052.

Cheng et al., (Journal of Obesity) vol. 2011, Article ID 984245 (2011).

International Search Report and Written Opinion from PCT/US15/22513, dated Jun. 17, 2015.

Extended European Search Report for EP 15769049, dated Oct. 30, 2017.

(Continued)

*Primary Examiner* — Patricia Duffy
*Assistant Examiner* — Garen Gotfredson
(74) *Attorney, Agent, or Firm* — Morse, Barnes-Brown & Pendleton, P.C.; Stanley F. Chalvire, Esq.

(57) ABSTRACT

Disclosed are pharmaceutical compositions and related methods for treating a subject with a viral or retroviral infection. The disclosed compositions and methods comprise and utilize an effective amount of one or more vanadium-containing compounds and an effective amount of one or more sulfonylureas. In certain embodiments, the viral infection is human immunodeficiency virus (HIV) and the compositions and methods improve one or more immunologic cellular parameters, such as viral load, CD4 counts and CD4/CD8 lymphocyte cell ratios in a subject. Also disclosed are methods of improving one or more immunologic cellular parameters that are associated with viral infections such as HIV in a subject, including viral load, CD4 counts and CD4/CD8 lymphocyte cell ratios.

18 Claims, 21 Drawing Sheets

(56) References Cited

OTHER PUBLICATIONS

Notice of Allowance and Fees Due in U.S. Appl. No. 15/129,339, dated Dec. 13, 2019.
Non-Final Office Action in U.S. Appl. No. 15/129,339, dated Aug. 21, 2019.
Final Office Action in U.S. Appl. No. 15/129,339, dated Jan. 24, 2019.
Non-Final Office Action in U.S. Appl. No. 15/129,339, dated Jul. 16, 2018.

* cited by examiner

COMPOSITIONS AND RELATED METHODS FOR RECONSTITUTING THE IMMUNE SYSTEM OF A SUBJECT

RELATED APPLICATIONS

This application is a continuation-in-part of, and claims priority to U.S. patent application Ser. No. 15/129,339, filed Sep. 26, 2016, which is a national stage filing under 35 U.S.C. § 371 of International Application No. PCT/US2015/022513, filed Mar. 25, 2015, which claims the benefit under 35 U.S.C. § 119(e) of U.S. Provisional Application Ser. No. 61/967,804, filed Mar. 26, 2014, the entire teachings of which are incorporated herein by reference.

FIELD OF THE INVENTION

The present inventions are generally directed to compositions and related methods of reconstituting and/or preventing the decompensated cellular immune system of a subject having a viral and/or retroviral infection, such as human immunodeficiency virus (HIV). In certain aspects, such compositions and related methods comprise one or more vanadium-containing compounds and one or more sulfonylureas.

BACKGROUND OF THE INVENTION

Vanadyl sulfate ($VOSO_4$), which is readily available over the counter in the United States at local health food stores, is marketed as a nutritional supplement. Although it may be useful for other purposes as well, vanadyl sulfate has historically been taken to improve glycemic control, as described, for example, in U.S. Pat. No. 5,885,980, the entire teachings of which are incorporated herein by reference. Vanadyl sulfate generates the vanadyl radical ($VO^{-3}$) which has been shown to reverse diabetes in pancreatectomized rats. The radical ($VO^{-3}$) is the predominant radical form that is present in extracellular fluid and is reduced intracellularly into the radical ($VO^{+2}$) which is the active form.

Although vanadium-containing compounds such as vanadyl sulfate, have been shown to produce dramatic therapeutic effects in animal models evaluating its effects on glucose metabolism, in human studies these observed effects have been exceedingly weak. It has been thought that inadequate cellular penetration into the human mammalian cell may contribute to the limited effects on glucose metabolism that have been observed in humans (Goldfine, et al., *J. Clin Endocrinol Metab*, 1995, 80(11): 3311-20; Boden, et al., *Metabolism*, 1996, 45(9): 1130-1135). Recently, vanadium has also been evaluated as a potential new class of anti-HIV agents (Wong, et al., *Chem. Commun.* (Cambridge), 2005 (28): 3544-3546), however, the virucidal activity of vanadium has not been demonstrated in humans and nor does such evaluation suggest how to address immune deterioration which occurs in human beings following, for example, HIV infection.

New therapeutic strategies are needed for the treatment of viral or retroviral infections such as HIV. Particularly needed are safe and effective compositions and methods for the treatment or eradication of viral and retroviral infections, while improving one or more immunologic cellular parameters associated with such infections.

SUMMARY OF THE INVENTION

The present inventions relate generally to pharmaceutical compositions and to related methods of treating or preventing viral and retroviral infections (e.g., human immunodeficiency virus (HIV)) or otherwise improving immunologic cellular parameters associated with such viral infections (e.g., improving viral load, CD4 counts and CD4/CD8 lymphocyte cell ratios in an HIV-positive subject). The inventions disclosed herein are especially suited for killing pathogens present in target infected cells. For example, in one embodiment the pathogen is a virus such as HIV, and the target infected cells are HIV infected cells.

Also disclosed herein are methods of treating or preventing a viral or retroviral infection in a subject (e.g., a human subject), wherein such methods comprise a step of administering to the subject an effective amount of a vanadium-containing compound (e.g., vanadyl sulfate) and an effective amount of a sulfonylurea (e.g., micronized glyburide), and thereby treating or preventing the viral or retroviral infection. For example, the methods disclosed herein can be practiced to treat or prevent a retroviral infection, such as human immunodeficiency virus (HIV) or acquired immunodeficiency syndrome (AIDS).

Certain immunologic cellular parameters such as, for example, CD4 counts and CD4/CD8 lymphocyte cell ratios, correlate closely with the presence of the pathogenic virus in a subject's body. Accordingly, in certain aspects, the methods disclosed herein are capable of improving one or more immunologic cellular parameters that are associated with a viral or retroviral infection. For example, such methods may be used or practiced to improve one or more immunologic cellular parameters selected from the group consisting of viral load, CD4 counts and CD4/CD8 lymphocyte cell ratios in the subject. Also disclosed are methods of reducing the viral load in a subject and methods of reducing or eliminating the reservoir of replication-competent provirions (e.g., HIV provirions) in a subject. For example, in certain embodiments the methods disclosed herein may be practiced to reduce the viral load in a subject (e.g., an HIV positive subject) to undetectable levels.

In certain aspects the methods disclosed herein comprise the administration of one or more sulfonylureas to the subject, which may be optionally micronized. For example, the sulfonylurea may be selected from the group consisting of glyburide, glipizide, glimepiride, gliclazide, glibenclamide, glibornuride, gliquidone, glisoxepide and glyclopyramide. In certain embodiments, the sulfonylurea is micronized (e.g., micronized glyburide). In certain aspects, an effective amount of the micronized glyburide is from about 0.75 mg to about 12 mg per day.

The methods disclosed herein further comprise the administration of one or more vanadium-containing compounds (e.g., vanadyl sulfate) to the subject (e.g., a mammalian subject). For example, in certain aspects, such vanadium-containing compounds are selected from the group consisting of sodium orthovanadate, sodium metavanadate, bis oxovanadium, sodium metavanadate, vanadyl sulfate, ammonium metavanadate, aluminum orthophosphate vanadia, diperoxovanadate, bis(maltolato)oxovanadium(IV), $VOCl_3$, $VOCl_{21}$, $VCl_3$, peroxovanadium compounds and combinations thereof. In some embodiments, the vanadium-containing compound comprises vanadyl sulfate. In some embodiments, an effective amount of the vanadyl sulfate is from about 10 mg to about 120 mg per day.

In some embodiments, the subject (e.g., a human subject) does not have diabetes. For example, a human subject having or suspected of having an active viral or retroviral infection (e.g., an HIV-positive subject) and that does not have diabetes mellitus may be co-administered one or more vanadium-containing compounds (e.g., vanadyl sulfate) and one or more sulfonylureas (e.g., glyburide).

In certain embodiments, the methods disclosed herein comprise the administration of one or more vanadium-containing compounds and one or more sulfonylureas to the subject for at least one month, at least two months, at least three months, at least four months, at least five months, at least six months, at least nine months, at least twelve months, at least eighteen months, at least twenty-four months, at least thirty-six months, at least forty-eight months or longer.

In certain aspects the methods disclosed herein may further comprise the co-administration of one or more antiviral or antiretroviral compounds to the subject. For example, an HIV-positive subject may be administered one or more vanadium-containing compounds and one or more sulfonylureas as an adjunct therapy that is administered in addition to a primary (e.g., primary antiviral or antiretroviral therapy) to maximize the effectiveness of such primary therapy. In certain embodiments where the subject (e.g., a human subject that does not have diabetes) is HIV-positive, the one or more vanadium-containing compounds and the one or more sulfonylureas may be administered in combination with one or more antiviral or antiretroviral compounds selected from the group consisting of lamivudine, zidovudine, lopinavir, ritonavir, abacavir, tenofovir, emtricitabine, efavirenz, rilpivirine, elvitegravir, cobicistat, dolutegravir, atazanavir, darunavir, raltegravir and any combinations thereof. In certain embodiments, such vanadium-containing compounds (e.g., vanadyl sulfate), sulfonylureas (e.g., micronized glyburide) and antiviral or antiretroviral compounds are administered to the subject in a fixed-dose combination or alternatively are co-packaged together to promote or otherwise improve patient compliance. In certain embodiments, the one or more vanadium-containing compounds and the one or more sulfonylureas may be administered in combination with highly active antiretroviral therapy (HAART).

Also disclosed herein are methods of treating or preventing human immunodeficiency virus (HIV) infection or acquired immunodeficiency syndrome (AIDS) in a subject (e.g., a human subject). Such methods comprise administering to the subject an effective amount of vanadyl sulfate and an effective amount of glyburide (e.g., micronized glyburide). In certain embodiments, such methods are capable of improving one or more immunologic cellular parameters that are associated with the viral or retroviral infection. For example, such methods may be used to improve one or more immunologic cellular parameters selected from the group consisting of viral load, CD4 counts and CD4/CD8 lymphocyte cell ratios in the subject. In certain embodiments, such methods further comprise administering one or more antiviral or antiretroviral compounds to the subject. In certain aspects, the subject does not have diabetes mellitus.

Pharmaceutical compositions for the treatment of a viral or retroviral infection in a subject are also disclosed herein. Also disclosed are pharmaceutical compositions for the treatment of a viral or retroviral infection in a subject. For example, in certain embodiments, such pharmaceutical compositions may be used to reduce or, in certain instances eliminate, the reservoir of replication-competent provirions (e.g., HIV provirions) in a subject. Additionally, disclosed herein are pharmaceutical compositions for reducing viral load in a subject. For example, in certain embodiments the pharmaceutical compositions disclosed herein may be administered to a subject reduce the subject's viral load to undetectable levels. In certain embodiments, such pharmaceutical compositions comprise an effective amount of a vanadium-containing compound (e.g., vanadyl sulfate), an effective amount of a sulfonylurea (e.g., glyburide) and a pharmaceutically acceptable carrier. The vanadium-containing compound may be selected from the group consisting of sodium orthovanadate, sodium metavanadate, bis oxovanadium, sodium metavanadate, vanadyl sulfate, ammonium metavanadate, aluminum orthophosphate vanadia, diperoxovanadate, bis(maltolato)oxovanadium(IV), $VOCl_3$, $VOCl_{21}$, $VCl_3$, peroxovanadium compounds and combinations thereof. The sulfonylurea may be selected from the group consisting of glyburide, glipizide, glimepiride, gliclazide, glibenclamide, glibornuride, gliquidone, glisoxepide and glyclopyramide. In certain aspects, such pharmaceutical compositions may further comprise an effective amount of one or more antiviral or antiretroviral compounds. For example, in certain aspects such pharmaceutical compositions may comprise one or more vanadium-containing compounds (e.g., vanadyl sulfate), one or more sulfonylureas (e.g., micronized glyburide) and one or more antiviral or antiretroviral compounds and such compositions may be formulated in a fixed-dose combination.

The above discussed, and many other features and attendant advantages of the present inventions will become better understood by reference to the following detailed description of the invention.

BRIEF DESCRIPTION OF THE DRAWINGS

The patent or patent application contains at least one drawing executed in color. Copies of this patent or patent application publication with color drawings will be provided by the Office upon request and payment of the necessary fee.

FIG. 1A illustrates the effect that the administered combination of a vanadium-containing compound and a sulfonylurea had on the subject's absolute CD4 count, expressed in cells/µL. FIG. 1B illustrates the effect that the administered combination of a vanadium-containing compound and a sulfonylurea had on the subject's viral load, as determined by quantifying plasma HIV-1 RNA by way of quantitative PCR and expressed in copies/mL. FIG. 1C illustrates the effects that the administered combination of a vanadium-containing compound and a sulfonylurea had on the subject's helper/suppressor (CD4/CD8) ratio. FIG. 1D illustrates the effects that the administered combination of a vanadium-containing compound and a sulfonylurea had on the subject's CD4 helper cells percentage.

FIG. 3A illustrates the effect that the administered combination of a vanadium-containing compound and a sulfonylurea had on the subject's absolute CD4 count, expressed in cells/µL. FIG. 3B illustrates the effects that the administered combination of a vanadium-containing compound and a sulfonylurea had on the subject's helper/suppressor (CD4/CD8) ratio. FIG. 3C illustrates the effects that the administered combination of a vanadium-containing compound and a sulfonylurea had on the subject's CD4 helper cells percentage. FIG. 3D illustrates the effect that the administered combination of a vanadium-containing compound and a sulfonylurea had on the subject's viral load, as determined by quantifying plasma HIV-1 RNA by way of quantitative PCR and expressed in copies/mL.

FIG. 4A illustrates the effect that the administered combination of a vanadium-containing compound and a sulfonylurea had on the subject's absolute CD4 count, expressed in cells/µL. FIG. 4B illustrates the effects that the administered combination of a vanadium-containing compound and a sulfonylurea had on the subject's helper/suppressor (CD4/CD8) ratio. FIG. 4C illustrates the effects that the administered combination of a vanadium-containing compound and a sulfonylurea had on the subject's CD4 helper cells percentage. FIG. 4D illustrates the effect that the administered combination of a vanadium-containing compound and a sulfonylurea had on the subject's viral load, as determined by quantifying plasma HIV-1 RNA by way of quantitative PCR and expressed in copies/mL.

FIG. 5A illustrates the effect that the administered combination of a vanadium-containing compound and a sulfonylurea had on the subject's absolute CD4 count, expressed in cells/µL. FIG. 5B illustrates the effects that the administered combination of a vanadium-containing compound and a sulfonylurea had on the subject's helper/suppressor (CD4/CD8) ratio. FIG. 5C illustrates the effect that the administered combination of a vanadium-containing compound and a sulfonylurea had on the subject's viral load, as determined by quantifying plasma HIV-1 RNA by way of quantitative PCR and expressed in copies/mL. FIG. 5D illustrates the effects that the administered combination of a vanadium-containing compound and a sulfonylurea had on the subject's CD4 helper cells percentage.

FIG. 6A illustrates the effect that the administered combination of a vanadium-containing compound and a sulfonylurea had on the subject's absolute CD4 count, expressed in cells/µL. FIG. 6B illustrates the effects that the administered combination of a vanadium-containing compound and a sulfonylurea had on the subject's helper/suppressor (CD4/CD8) ratio. FIG. 6C illustrates the effects that the administered combination of a vanadium-containing compound and a sulfonylurea had on the subject's CD4 helper cells percentage. FIG. 6D illustrates the effect that the administered combination of a vanadium-containing compound and a sulfonylurea had on the subject's viral load, as determined by quantifying plasma HIV-1 RNA by way of quantitative PCR and expressed in copies/mL.

FIGS. 7A-F illustrates the effect that the administered antiretroviral medications had on the subject's absolute CD4 count, expressed in cells/µL. FIGS. 7G-J illustrate improvements in immune cellular parameters that were observed in an HIV-positive subject that was administered standard antiretroviral medications without the combination of a vanadium-containing compound and a sulfonylurea. FIG. 7G illustrates the effects that the administered antiretroviral medications had on the subject's helper/suppressor (CD4/CD8) ratio. FIG. 7H illustrates the effects that the administered antiretroviral medications had on the subject's CD4 helper cells percentage. FIGS. 7I-J illustrate the effect that the administered antiretroviral medications had on the subject's viral load, as determined by quantifying plasma HIV-1 RNA by way of quantitative PCR and expressed in copies/mL.

FIG. 8A illustrates the effect that the administered combination of a vanadium-containing compound and a sulfonylurea had on the subject's absolute CD4 count, expressed in cells/µL. FIG. 8B illustrates the effects that the administered combination of a vanadium-containing compound and a sulfonylurea had on the subject's helper/suppressor (CD4/CD8) ratio.

FIG. 9A illustrates the effect that the administered combination of a vanadium-containing compound and a sulfonylurea had on the subject's absolute CD4 count, expressed in cells/µL. FIG. 9B illustrates the effects that the administered combination of a vanadium-containing compound and a sulfonylurea had on the subject's helper/suppressor (CD4/CD8) ratio.

FIG. 10A illustrates the effect that the administered combination of a vanadium-containing compound and a sulfonylurea had on the subject's absolute CD4 count, expressed in cells/µL. FIG. 10B illustrates the effects that the administered combination of a vanadium-containing compound and a sulfonylurea had on the subject's helper/suppressor (CD4/CD8) ratio. FIG. 10C illustrates the effect that the administered combination of a vanadium-containing compound and a sulfonylurea had on the subject's absolute CD8 count, expressed in cells/µL.

FIG. 11A illustrates the effect that the administered combination of a vanadium-containing compound and a sulfonylurea had on the subject's absolute CD4 and CD8 counts, expressed in cells/μL. and on the subject's viral load, as determined by quantifying plasma HIV-1 RNA. FIG. 11B illustrates the effects that the administered combination of a vanadium-containing compound and a sulfonylurea had on the subject's percentages of helper and suppressor (CD4/CD8) T-cells, and on the subject's viral load, as determined by quantifying plasma HIV-1 RNA. FIG. 11C illustrates the effects that the administered combination of a vanadium-containing compound and a sulfonylurea had on the subject's helper/suppressor (CD4/CD8) ratio, and on the subject's viral load, as determined by quantifying plasma HIV-1 RNA. FIG. 11D illustrates the effects that the administered combination of a vanadium-containing compound and a sulfonylurea had on the subject's absolute lymphocytes and on the subject's viral load. FIGS. 11E and 11F illustrate the effects that the administered combination of a vanadium-containing compound and a sulfonylurea had on the subject's platelets and white blood cells, respectively, and on the subject's viral load. As evidenced by such figures, these other cell lines from the hematopoietic system also improved simultaneously and concordantly, suggesting restoration of the hematopoietic system and the recovery of CD34 hematopoietic stem cell function.

FIG. 12A illustrates the effect that the administered combination of a vanadium-containing compound and a sulfonylurea had on the subject's absolute CD4 and CD8 counts, expressed in cells/μL, and on the subject's viral load, as determined by quantifying plasma HIV-1 RNA. FIG. 12B illustrates the effects that the administered combination of a vanadium-containing compound and a sulfonylurea had on the subject's percentages of helper and suppressor (CD4/CD8) T-cells, and on the subject's viral load, as determined by quantifying plasma HIV-1 RNA. FIG. 12C illustrates the effects that the administered combination of a vanadium-containing compound and a sulfonylurea had on the subject's helper/suppressor (CD4/CD8) ratio, and on the subject's viral load, as determined by quantifying plasma HIV-1 RNA. FIG. 12D illustrates the effects that the administered combination of a vanadium-containing compound and a sulfonylurea had on the subject's absolute lymphocytes and on the subject's viral load. FIGS. 12E and 12F illustrate the effects that the administered combination of a vanadium-containing compound and a sulfonylurea had on the subject's platelets and hemoglobin, respectively, and on the subject's viral load.

DETAILED DESCRIPTION OF THE INVENTION

Figures 1A, 1B, 1C, 1D:
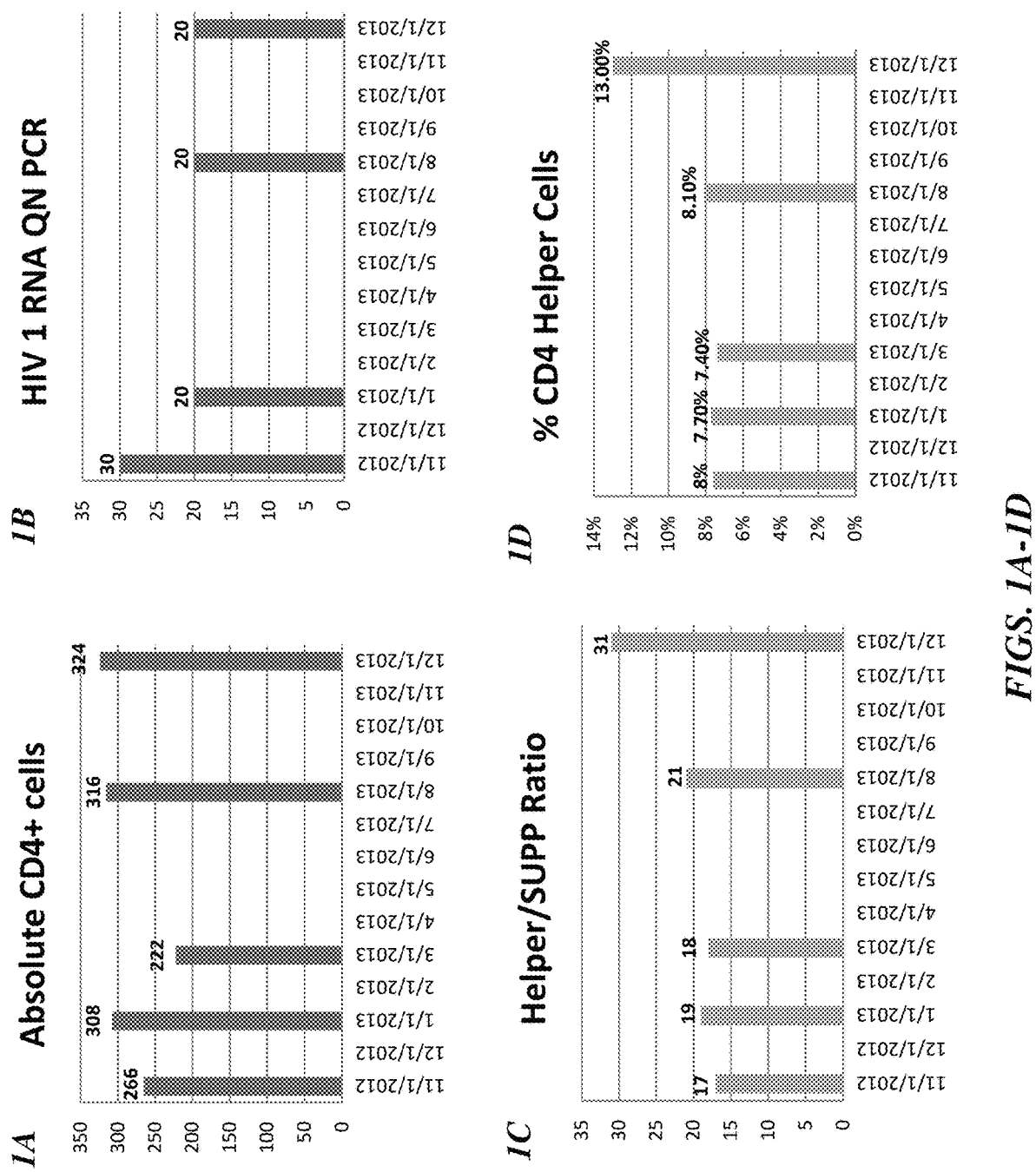
FIGS. 1A-D demonstrate the improvements in immune cellular parameters that were observed in an HIV-positive subject that was administered a combination of a vanadium-containing compound and a sulfonylurea.

The present inventions are generally directed to compositions (e.g., pharmaceutical compositions) and to related methods of treating viral or retroviral infections, such as human immunodeficiency virus (HIV) and acquired immune deficiency syndrome (AIDS), and to improving certain immunologic cellular parameters that may be associated with such viral infections (e.g., CD4 counts and CD4/CD8 lymphocyte cell ratios in an HIV-positive subject). The inventions disclosed herein are particularly suited for killing pathogens (e.g., viral pathogens) that may be present in an infected cell. For example, in certain embodiments the present invention may be used to kill a viral pathogen such as HIV, by targeting cells that are infected with the HIV virus.

In certain embodiments, the compositions and methods disclosed herein generally comprise a combination of an effective amount of one or more vanadium-containing compounds (e.g., vanadyl sulfate) and an effective amount of one or more sulfonylureas (e.g., micronized glyburide). As used herein, the term "vanadium-containing compound" is intended to encompass any compounds which form or produce the vanadium oxide $VO^{+2}$ radical in, for example, a subject's body or cells. In certain embodiments, the vanadium-containing compound (e.g., vanadyl sulfate) forms such $VO^{+2}$ radical intracellularly upon or following its administration (e.g., oral or parenteral administration) to a subject. It is believed that the $VO^{-3}$ radical is reduced after entry into the cells to yield the radical $VO^{+2}$. Since vanadium readily changes oxidation state, it is preferred to describe the therapeutic amounts of vanadium-containing compounds on the basis of the weight of the element vanadium.

Vanadium inhibits the $(Na^{++}K^+)$-ATPase enzyme and the $Na^+$, $K^+$ pump and has been shown to bind to the phosphate residue of the $(Na^{++}K^+)$-ATPase enzyme. It has been shown that vanadate exerts its activity through the sulfonylurea receptor subunit (Proka, et al. *J. Biol. Chem.*, 1999, 274(36): 25393-25397). Exemplary vanadium-containing compounds include, without limitation, sodium orthovanadate, sodium metavanadate, bis oxovanadium, sodium metavanadate ($NaVO_3$), vanadyl sulfate ($VOSO_4$), sodium orthovanadate ($Na_3 VO_4$), ammonium metavanadate($NH_4VO_3^-$), aluminum orthophosphate vanadia ($V_2O_5^-AlPO_4$), diperoxovanadate, bis(maltolato)oxovanadium(IV) (BMOV), $VOCl_3$, $VOCl_{21}$ VCb, peroxovanadium (pv)compounds, $K_2[VO(O_2)_2$ (picolinato)]2 $H_2O)[bpv(pic)]$ $VO(O_2)(picolinato)(H_2O)2$ [MPV(pic)], and the like. In certain embodiments, the preferred vanadium-containing compound is vanadyl sulfate due to its lower levels of toxicity relative to other vanadium-containing compounds.

The compositions and methods disclosed herein also generally comprise an effective amount of one or more sulfonylureas such as, for example, glyburide. In certain embodiments, the sulfonylurea is micronized (e.g., micronized glyburide) or is characterized by small particle sizes in the micron range. Exemplary sulfonylureas include, without limitation, glyburide, glipizide, glimepiride, gliclazide, glibenclamide, glibornuride, gliquidone, glisoxepide and glyclopyramide, any of which may be optionally micronized. Sulfonylureas such as glyburide bind firmly to the 140 kda protein of the potassium channel, also referred to as the sulfonylurea receptor. Glyburide is the most biochemically-potent stimulator of the sulfonylurea receptor because of the characteristic of its constant action associated to its firm binding to the sulfonylurea receptor deep at the 140 kda protein site.

As used herein, the term "effective amount" means an amount sufficient to achieve a meaningful benefit to the subject (e.g., treating, modulating, curing, preventing and/or ameliorating the underlying viral disease). For example, an effective amount of the vanadium-containing compounds that are the subject of the present inventions may be generally determined based on the activity of such compounds and the amount of such compounds that are absorbed by the subject following its oral administration. Generally, the amount of compound administered to a subject in need thereof will depend upon the characteristics of the subject and the severity of their disease. Such characteristics include the condition, general health, age, subjective symptoms, objective appearance, sex and body weight of the subject.

An effective amount of a vanadium-containing compound (e.g., vanadyl sulfate) necessary to treat viral or retroviral infections in accordance with the present inventions is generally in the range of from about 30 mg/day to 120 mg/day, or preferably from about 60 mg/day to 120 mg/day for a human subject of standard body weight (e.g., 150-160 pounds). One of ordinary skill in the art will be readily able to determine an effective amount depending on these and other related factors. For example, vanadyl sulfate ($VOSO_4$) can generally be administered in an amount of from about 10 mg/day to 120 mg/day, preferably from about 30 mg/day to 90 mg/day, and most preferably from about 60 mg/day to 90 mg/day. The required dosage amount may be administered once, twice, three times, four times or up to several times a day. In certain embodiments, an effective amount of a vanadium-containing compound is administered to the subject at least once a day (e.g., 60 mg of vanadyl sulfate once daily).

An effective amount of a sulfonylurea (e.g., micronized glyburide) necessary to treat viral or retroviral infections in accordance with the present inventions is generally in the range of from about 0.75 mg/day to 12 mg/day, preferably from about 1.25 mg/day to 9 mg/day, most preferably from about 3 mg/day to 7.5 mg/day for a human subject of standard body weight (e.g., 150-160 pounds). Micronized glyburide may be administered in accordance with the present invention as a single dose or up to four times daily, preferably in one dose with the vanadium-containing compound as previously described.

The one or more vanadium-containing compounds (e.g., vanadyl sulfate) and one or more sulfonylurea (e.g., micronized glyburide) may be co-administered in separate dosage forms, or formulated in a fixed-dose combination dosage form. In those embodiments where the vanadium-containing compound and sulfonylurea are co-administered separately, preferably such agents are administered at or about the same time. In those embodiments where an effective amount of the vanadium-containing compound and sulfonylurea are formulated into a single pharmaceutical composition, such composition may be formulated for oral administration (e.g., in the form of tablets, capsules, caplets, soft gel capsules and the like).

The combination of the vanadium-containing compound and sulfonylurea (e.g., micronized glyburide) may be administered to the subject over a period of up to 9 months or longer, preferably from about 3 weeks to 9 months, and most preferably from about 6 months to 9 months. Shorter or longer periods of treatment can be employed depending on the subject's response (e.g., by observing improvements in one or more of the subject's immunologic cellular parameters, such as the subject's absolute CD4 cell count). Once the desired response is achieved the combination of the vanadium-containing compound and the sulfonylurea can be administered indefinitely without any significant adverse or side effects.

In addition to treating viral or retroviral infections (e.g., HIV), the compositions and methods disclosed herein may be used to improve one or more immunologic cellular parameters that are associated with such a viral infection (e.g., absolute CD4 cell counts and CD4/CD8 lymphocyte cell ratios) or that otherwise correlate with the presence of a pathogenic virus in the subject's body. As used herein, the phrase "immunologic cellular parameters" generally refers to any immunologic and/or hematological objective parameters that may be used to assess or monitor a subject's condition (e.g., a viral or retroviral infection), the progression of disease and/or the efficacy of the inventions disclosed herein. In certain embodiments (e.g., where the retroviral infection is HIV), the immunologic cellular parameters are selected from the group consisting of CD4 counts and CD4/CD8 lymphocyte cell ratios. In certain embodiments, the phrase "immunologic cellular parameters" includes a subject's viral load and accordingly, in such embodiments, the immunologic cellular parameters are selected from the group consisting of viral load, CD4 counts and CD4/CD8 lymphocyte cell ratios. As used herein, the term "viral load" refers to the concentration or number of copies of a virus (e.g., HIV) detected in the blood or serum of a subject. In certain embodiments where the subject is HIV-positive, the compositions and methods disclosed herein reduce or eliminate a subject's viral load. In certain embodiments, the compositions and methods disclosed herein reduce or eliminate the reservoir of replication-competent provirions that may persist during treatment with highly active antiretroviral therapy (HAART) within the CD4 T-cells and which contribute to the disease burden. For example, in certain embodiments the compositions and methods disclosed herein may be used to reduce an HIV-positive subject's viral load to undetectable levels. Similarly, in certain embodiments the compositions and methods disclosed herein may be used to reduce or eliminate the reservoir of replication-competent provirions (e.g., HIV provirions) to undetectable levels.

In a preferred embodiment of the present invention, the method of improving immunologic cellular parameters includes administering to the subject of from about 60 mg to 90 mg of vanadyl sulfate and 3 mg to 12 mg of micronized glyburide once daily, preferably in the morning for at least 8 weeks and up to 9 months until a response is noted with normalization of immunologic cellular parameters including CD4 counts and CD4/CD8 lymphocyte cell ratios at the normal or near normal ranges.

The active agents of the present invention (e.g. vanadyl sulfate and micronized glyburide) are commercially available and can be utilized as such in the present invention. However, if fixed combination dosages forms are desired, they may be formulated by grinding each of the commercially available components together and placing the appropriate amount of the combination in an appropriate dosage delivery form (e.g. capsule or tablet) by known techniques. Alternatively, the active components may be optionally mixed along with pharmaceutically acceptable carriers (e.g. cornstarch, lactose, lecithin, soybean oil, glycerine and the like) as desired, and the mixture put up into an appropriate dosage form. The methods of preparing the pharmaceutical compositions of the present invention and selection of pharmaceutically acceptable carriers and excipients are described in detail in, for example, L. William, Remington: The Science and Practice of Pharmacy. $22^{nd}$ ed. Pharmaceutical Press (2012), the entire contents of which are incorporated herein by reference. In a preferred embodiment of the present invention, the pharmaceutical composition is formulated into a dosage form (e.g., a tablet or capsule) comprising 3 mg glyburide and 60 mg vanadyl sulfate.

It should be noted that the pharmaceutical compositions disclosed herein may be administered to a subject via any suitable route of administration, including one or more of the topical, transdermal, buccal, sublingual, oral or parenteral routes of administration. In certain embodiments, such pharmaceutical compositions may be administered to a subject orally. In certain other embodiments, such pharmaceutical compositions are administered to a subject intravenously.

The compositions and methods disclosed herein may be administered alone or as an adjunct therapy in combination with antiviral or antiretroviral compounds. For example, in those embodiments where the compositions and methods of the present invention are used to treat an HIV-positive subject, such compositions and methods may be administered in combination with antiretroviral therapy (e.g., in a combination with a combination of at drugs that suppress HIV replication). In certain embodiments, the composition and methods disclosed herein are administered in combination with HAART. For example, one or more vanadium-containing compounds and one or more sulfonylureas may be administered, formulated or packaged in combination with one, two, three or more antiviral or antiretroviral compounds selected from the group consisting of lamivudine, zidovudine, lopinavir, ritonavir, abacavir, tenofovir, emtricitabine, efavirenz, rilpivirine, elvitegravir, cobicistat, dolutegravir, atazanavir, darunavir, raltegravir and any combinations thereof.

While in certain embodiments, the inventions disclosed herein contemplate the treatment of viral or retroviral infections such as HIV and AIDS, it should be understood that the utility of such inventions are not limited to HIV. Rather, the compositions and methods disclosed herein are useful for treating any viral or retroviral infections. For example, in certain embodiments, the compositions and methods disclosed herein may be used for the treatment of one or more of Dengue fever, Japanese encephalitis, West Nile encephalitis, Yellow fever, Hepatitis C, Epstein-Barr virus, Ebola virus, Herpes simplex virus 1 and 2, respiratory syncytial virus, influenza, human papillomavirus and others. In such embodiments, the inventions disclosed herein may also be administered in combination with standard antiviral or antiretroviral compounds or medications.

It is to be understood that the invention is not limited in its application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

While certain compounds, compositions and methods of the present invention have been described with specificity in accordance with certain embodiments, the following examples serve only to illustrate the methods and compositions of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

AB is 59-year-old man who was diagnosed as being HIV-positive on Jul. 18, 2011. At the time of diagnosis AB had advanced immunosuppression and *Pneumocystis carinii* pneumonia (PCP). AB's CD4% count was 2.3%, his absolute CD4 count was 18 cells/µL, his CD4/CD8 ratio was 0.1, and his viral load was 325,444 copies/mL.

AB was originally placed on a fixed-dose combination of emtricitabine, tenofovir and ATRIPLA (efavirenz) in September 2011. In December 2012, AB's therapy was changed to TRUVADA (tenofovir, emtricitabine) and SUSTIVA (efavirenz), yet his immune system remained in a decompensated state. In March 2013, AB was prescribed and began taking 6 mg of micronized glyburide twice daily and 30 mg of vanadyl sulfate daily for 4 months without improvement in immunologic cellular parameters, at which point the administered dose of vanadyl sulfate was increased to 60 mg daily, resulting in the observed improvement of immunologic cellular parameters, as shown in FIGS. 1A-1D.

As illustrated in FIGS. 1A-1D, within months of initiating therapy with micronized glyburide and vanadyl sulfate, dramatic improvements in immune cellular parameters were observed. The observed improvements in AB's CD4 counts and CD4/CD8 ratio suggest that the administered combination of micronized glyburide and vanadyl sulfate produced a profound positive effect on AB's immune health and further suggest depletion of HIV virus reservoirs due to intracellular killing of the virus.

Example 2

DC is a 63-year-old woman who was diagnosed as being HIV-positive in 1989 and subsequently developed AIDS in 2000. DC observed several of her friends suffer from complications related to antiviral therapies and, as a result she has been non-compliant with prescribed antiviral therapy. DC has historically complied with prescribed antiviral therapy for a maximum period of approximately two to three months at a time and usually remains non-compliant to antiviral therapy for a period of several months (anywhere from 3 months to 6 months) at a time, until she begins to develop severe lymphadenopathy, thrush or opportunistic infections. To avoid opportunistic infections, DC is continually using antifungals and antibiotics. As a result of DC's non-compliance, the HIV virus has become resistant to numerous antiviral therapies, including integrase inhibitors such as raltegravir. When she does comply with her prescribed antiviral therapy, she has admitted to only taking half of the prescribed dose of the medications ISENTRESS (raltegravir), INTELENCE (etravirine) and EPIVIR (lamivudine).

Adjunct therapy with micronized glyburide and vanadyl sulfate was initiated, however until about July 2013, DC did not comply with the prescribed therapy and instead elected to use only one of the two prescribed components. The results of her action revealed a reduction in her viral load, however her cell counts remained exceedingly diminished, keeping DC in severe immunologic failure. DC has had AIDS for 14 years while having the disease for 30 years, a case of immune senescence. Her virus counts decreased from 8,087 copies to 500 copies within several weeks of having initiated adjunct therapy with micronized glyburide and vanadyl sulfate. The reduction in virus counts which occurred in the extracellular compartment suggested a direct viricidal action of the vanadium component because there was no improvement in the immune cell counts.

Figures 2A, 2B:
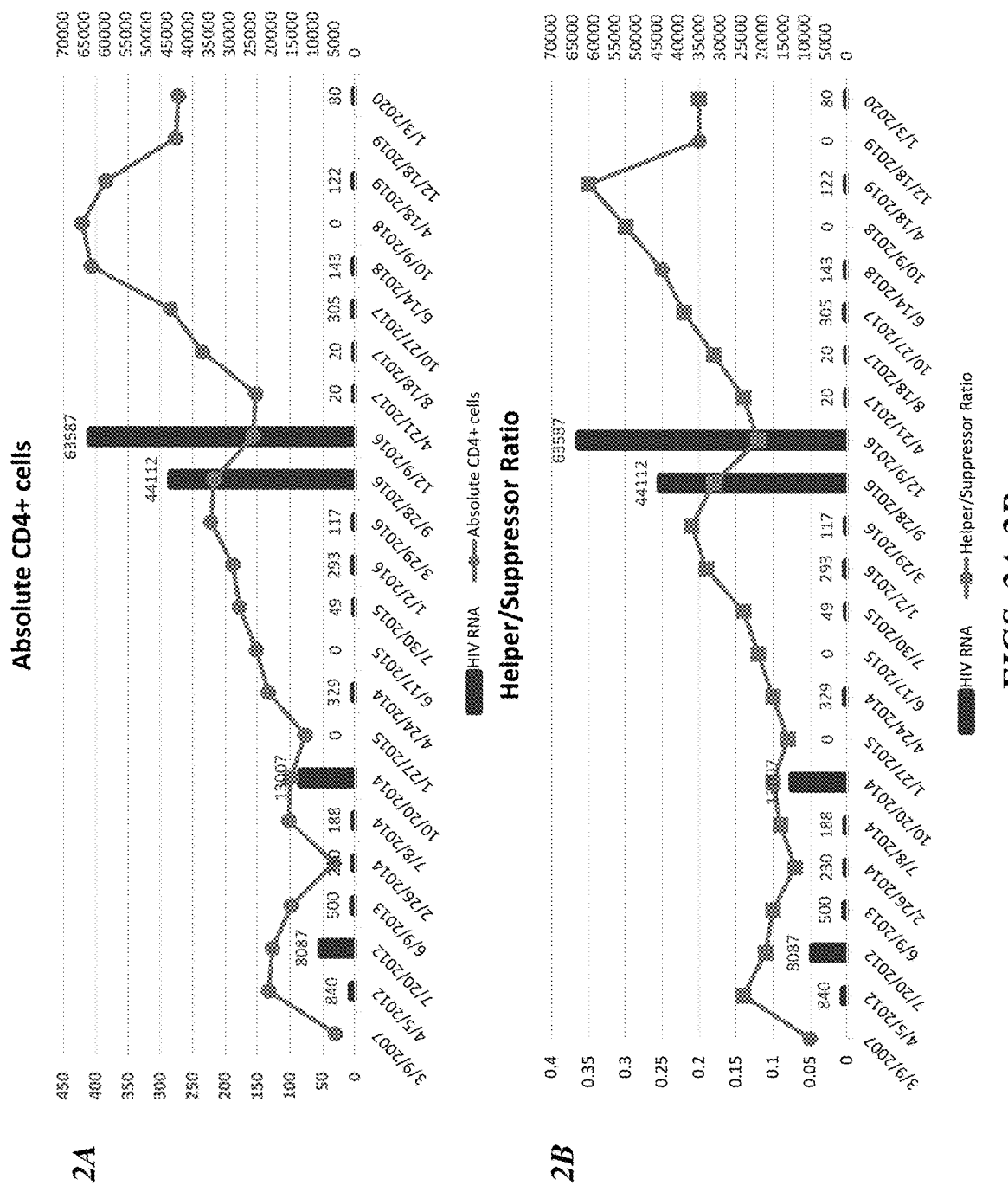
FIGS. 2A-2B illustrate improvements in a subject's absolute CD4+ cell counts, viral load and helper/suppressor (CD4/CD8) ratio observed in an HIV-positive subject that was administered standard antiretroviral medications with the combination of a vanadium-containing compound and a sulfonylurea. During the fall of 2019, the subject discontinued prescribed antiviral and adjunct therapies for a four-month period and, as shown in FIG. 2A and FIG. 2B, on Dec. 18, 2019, during a hospitalization, her virus measurement was undetectable. Notably, the subject's CD4 counts dropped to 275 cells/µL; however in spite of this drop, the virus counts remained undetectable. On prior occasions when discontinuing therapy, the subject has developed viremia followed by marked reductions in CD4 cell counts as well as CD4/CD8 ratios. The expected viral rebound counts would be expected to occur within days of discontinuing the therapy, and a delayed rebound time is considered a reflection of a decreased viral reservoir.

In March 2014, DC complied with the recommended therapy and, as illustrated in FIG. 2A, her CD4 counts increased in a few months from 32 to 102 cells/µL. Later, as DC continued to comply, she came out of the AIDS status once her CD4 cell counts exceeded 200 cells/µL. There was a reduction in cell counts during September and October 2016, due to DC's having discontinued all prescribed antiviral therapies, however the drop in immune cell counts was attenuated.

Based on the observed prolonged rebound time and persistent increases in CD4/CD8 ratios foregoing observations, the present inventor submits that the prescribed adjunct therapy decreased the provirus reservoir and disrupted the virus' capacity for replication.

Example 3

HH is a 31-year-old woman and has been HIV-positive for over ten years. HH had a history of non-compliance with prescribed antiviral therapy and had developed anti-retroviral resistance. After having been without treatment for several months, HH presented for care in November 2012, prior to which she stated had been treated with a fixed-dose combination of ATRIPLA (emtricitabine, tenofovir, efavirenz).

HH was not responding to her antiviral therapy and was empirically started on a fixed-dose combination of TRUVADA (tenofovir, emtricitabine) and SUSTIVA (efavirenz) in July 2013. HH's immunologic competence continued deteriorating and in April 2014, HH was placed on opportunistic infection prophylaxis for immunologic failure. HH was then placed on EPZICOM (abacavir sulfate), NORVIR (ritonavir) and PREZISTA (darunavir) in May 2014. At this time adjunct therapy with 3 mg micronized glyburide and 60 mg vanadyl sulfate was also initiated.

Figures 3A, 3B, 3C, 3D:
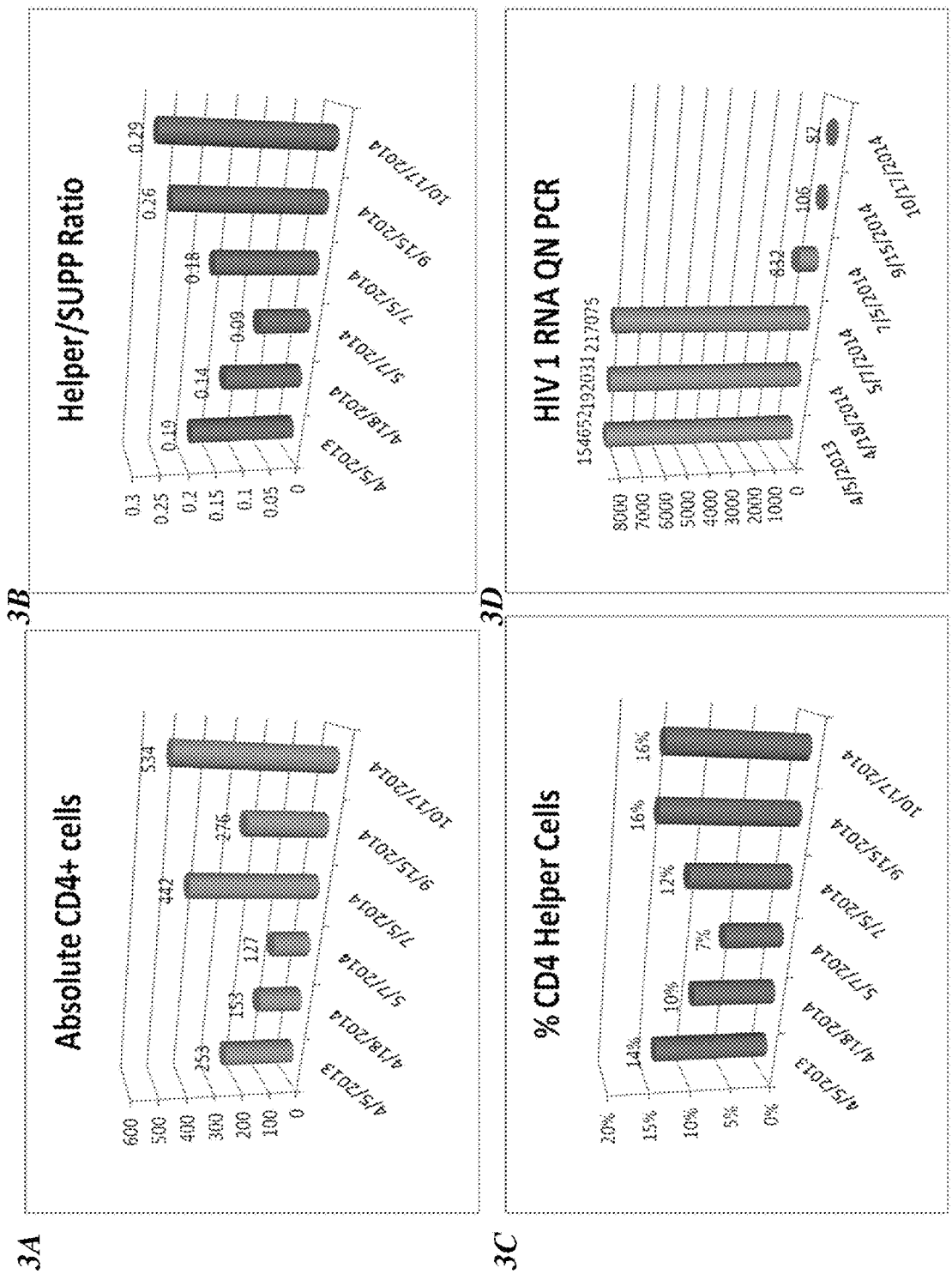
FIGS. 3A-D illustrate the improvements in immune cellular parameters that were observed in an HIV-positive subject that was administered a combination of a vanadium-containing compound and a sulfonylurea.

As illustrated in FIGS. 3A and 3D, within approximately one month, HH's absolute CD4 lymphocyte count increased from 127 cells/µL to 442 cells/µL, while her viral load dropped from 217,075 copies to 832 copies. Under conventional antiretroviral therapy the observed improvements in cell counts are perhaps 10 to 100-fold slower that those observed in the present study. The foregoing therefore suggests that since therapy with micronized glyburide and vanadyl sulfate involves a nonspecific virucidal agent with genomic actions with a cellular transport system, the vanadium-containing vanadyl sulfate may be destroying the provirions in the intracellular reservoirs and the free virus in the blood stream.

Example 4

WM a 47-year-old man who presented for care in June 2014, upon released from a one-month hospitalization due to respiratory failure resulting from to *Pneumocystis carinii* pneumonia (PCP), where he was newly diagnosed with symptomatic AIDS. Therapy with 6 mg micronized glyburide and 60 mg vanadyl sulfate was also proposed and initiated at this time to reconstitute his immune system and avoid opportunistic infections.

Figures 4A, 4B, 4C, 4D:
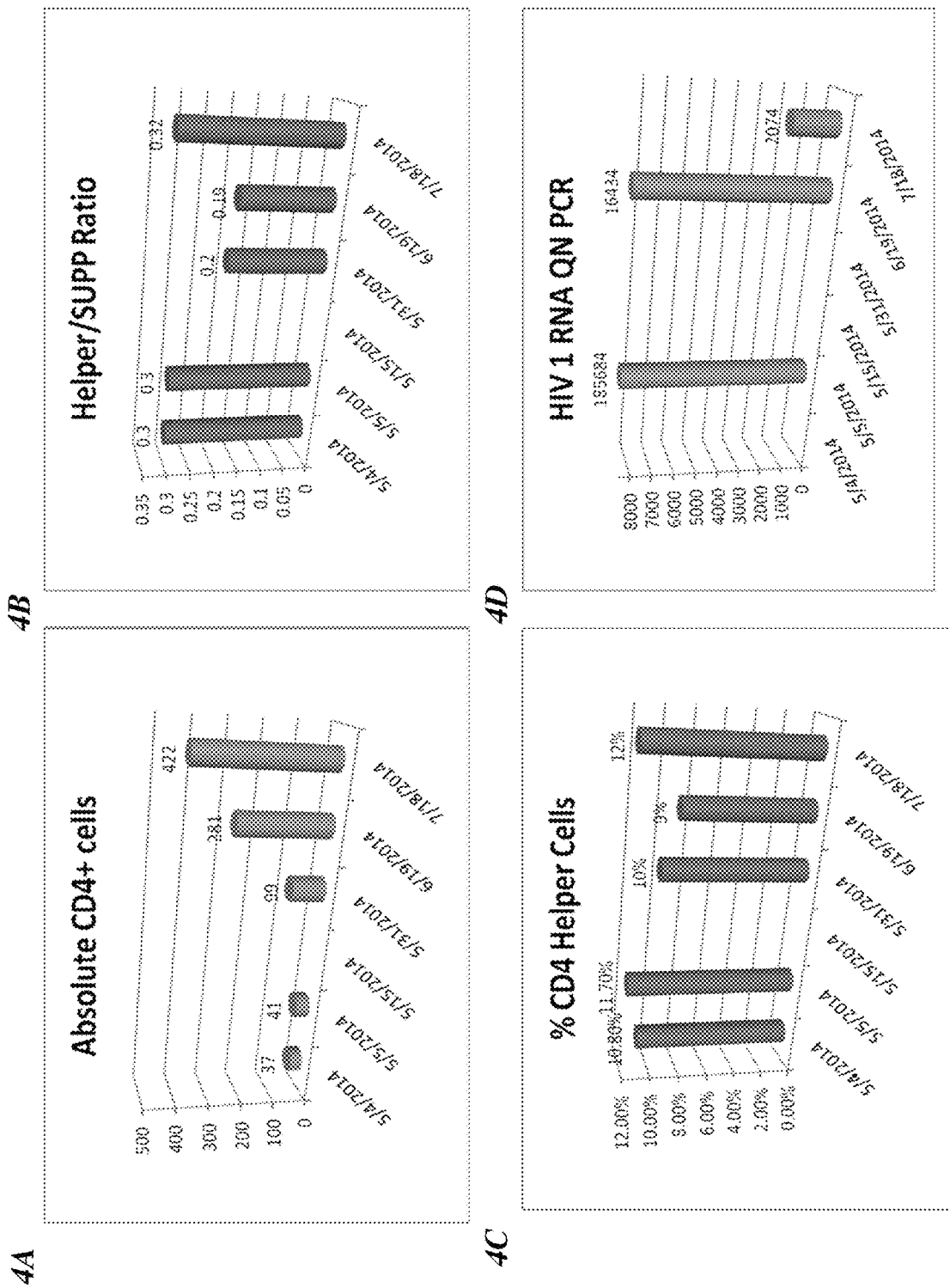
FIGS. 4A-D illustrate the improvements in immune cellular parameters that were observed in an HIV-positive subject that was administered a combination of a vanadium-containing compound and a sulfonylurea.
Figures 5A, 5B, 5C, 5D:
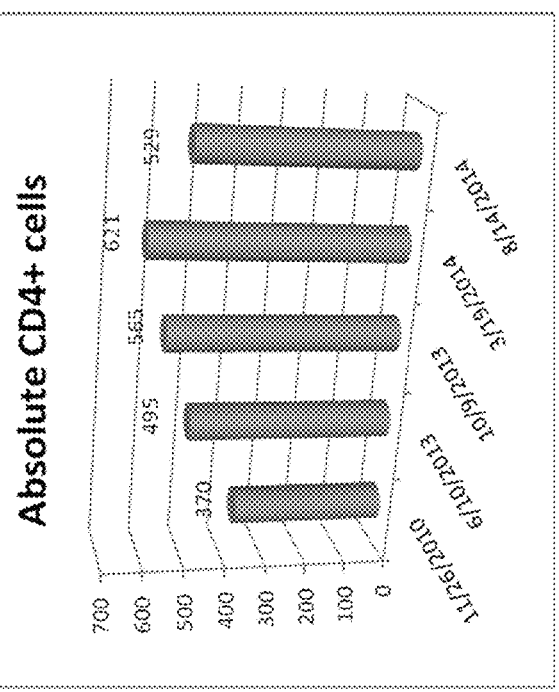
FIGS. 5A-D illustrate the improvements in immune cellular parameters that were observed in an HIV-positive subject that was administered a combination of a vanadium-containing compound and a sulfonylurea.
Figure 6A:
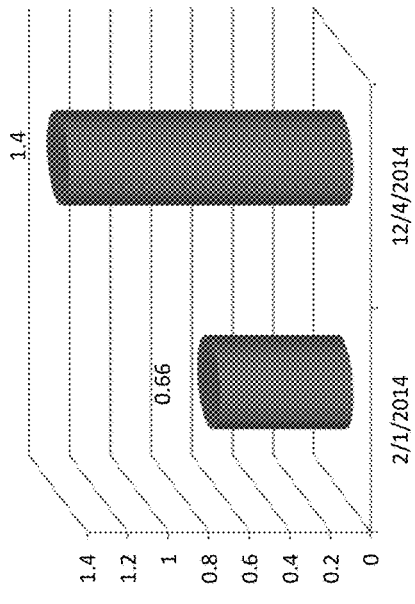
FIGS. 6A-D illustrate the improvements in immune cellular parameters that were observed in an HIV-positive subject that was administered a combination of a vanadium-containing compound and a sulfonylurea.
Figure 6B:
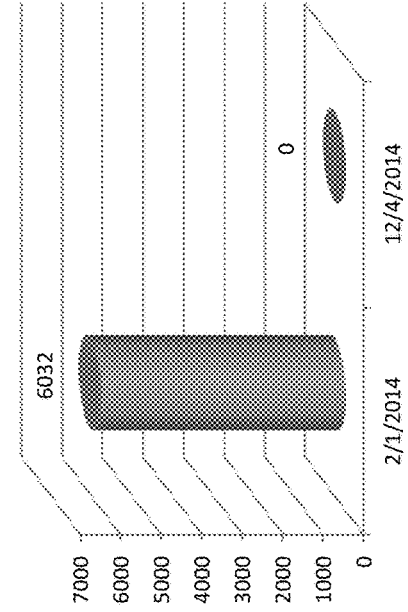
Figure 6C:
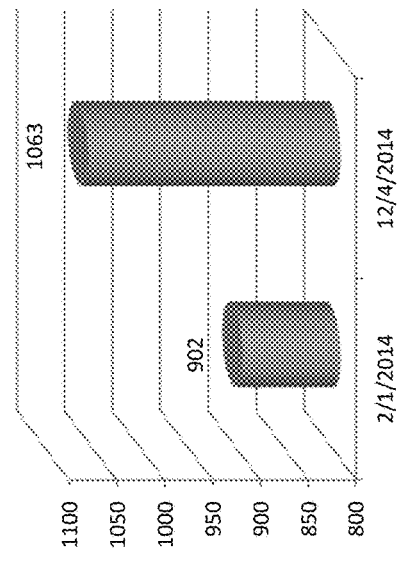
Figure 6D:
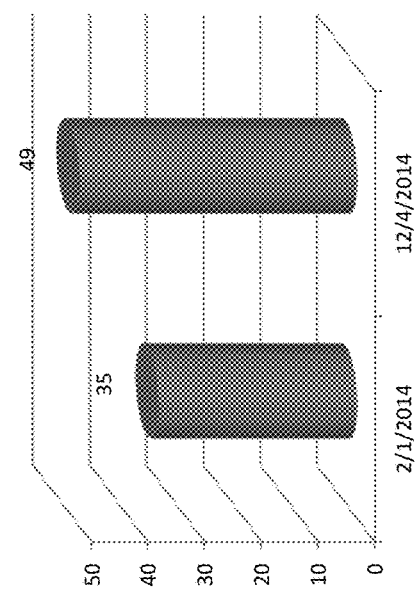

As illustrated in FIG. 4A, a marked improvement in WM's absolute CD4 lymphocyte counts from 288 cells/µL to 422 cells/µL was observed within one month of having initiating therapy with micronized glyburide and vanadyl sulfate. Similarly, as illustrated in FIG. 4D, a reduction in WM's viral load from 16,434 copies to 2,074 copies was observed within one month of initiating therapy. The rapid and almost complete restoration of the immune system that was observed following the initiation of therapy with micronized glyburide and vanadyl sulfate could not have resulted from only inhibition of HIV viral replication by the antiretroviral medications, but rather suggests direct virucidal actions by such therapy at the genomic level.

Example 5

TW is a 44-year-old man who presented for care in March 2013 with a twenty-year history of HIV and who had been undergoing antiretroviral treatment since 2010. TW had achieved appropriate viral suppression yet his immune system remained impaired and had remained this way for many years.

Adjunct therapy with 3 mg micronized glyburide and 60 mg vanadyl sulfate was also proposed and initiated. As illustrated in FIGS. 5A-5D, since having initiated such adjunct therapy TW has experienced a steady and consistent improvement in his immune cellular parameters. In particular, the observed normalization of his CD4 lymphocyte counts (FIG. 5A) and significant improvements in his CD4/CD8 ratio (FIG. 5B) suggest depletion of viral reservoirs.

Example 6

PL is a 43-year-old woman newly diagnosed as being HIV-positive and who presented for care in October 2014. PL has had a positive response to standard antiretroviral therapy with emtricitabine, rilpivirine, and tenofovir (COMPLERA), yet her immune cellular parameters were not optimal.

Adjunct therapy with 3 mg of micronized glyburide and 60 mg of vanadyl sulfate was also proposed and initiated in October 2014 and, within 2 months significant improvement in immune cellular parameters were observed, as illustrated in FIGS. 6A-6D. PL has continued the adjunct therapy without any adverse effects or hypoglycemia even though she is not a diabetic.

Example 7

JB is an HIV-positive male subject who presented for care after having previously received standard medical treatment with antiretroviral medications from another clinic. JB had not been prescribed a course of micronized glyburide and vanadyl sulfate.

Figures 7A, 7B, 7C, 7D, 7E, 7F:
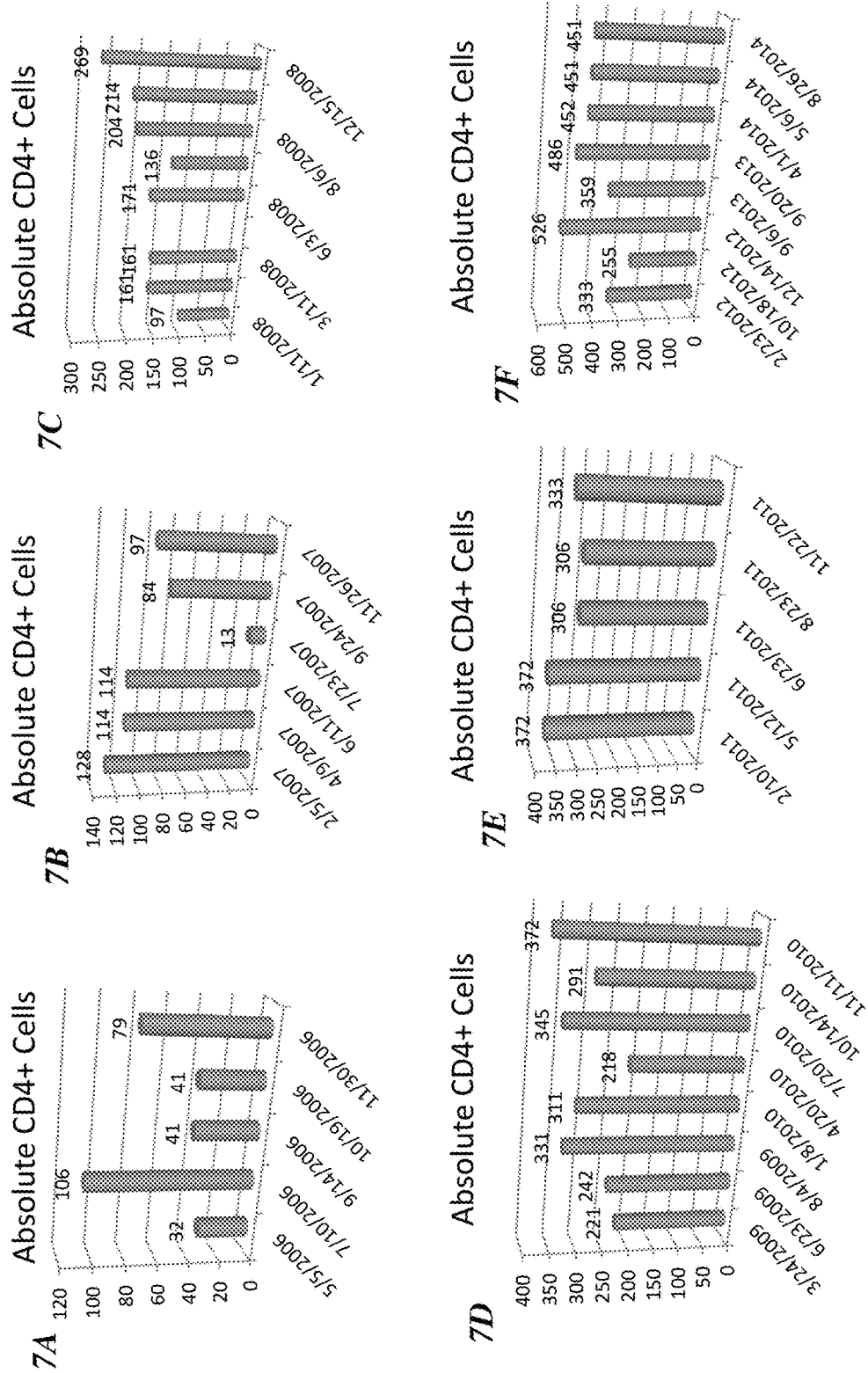
FIGS. 7A-J illustrate improvements in immune cellular parameters that were observed in an HIV-positive subject that was administered standard antiretroviral medications without the combination of a vanadium-containing compound and a sulfonylurea. In particular.
Figure 7G:
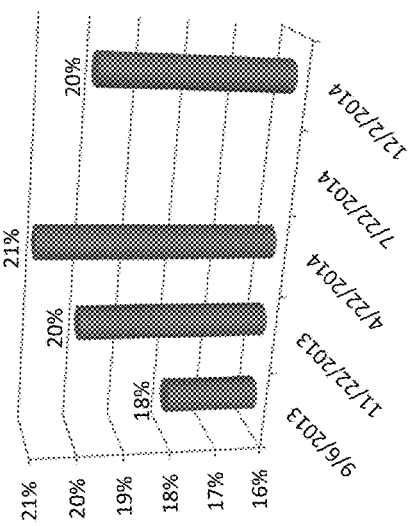
Figure 7H:
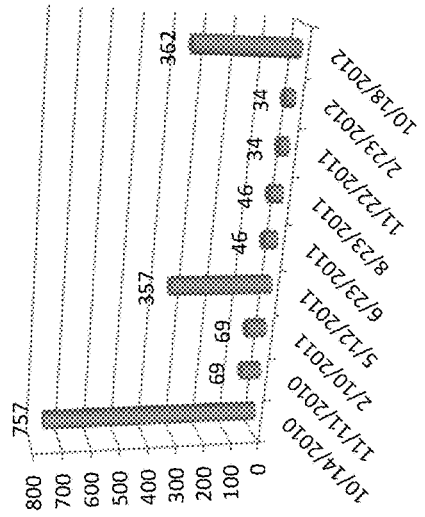
Figure 7I:
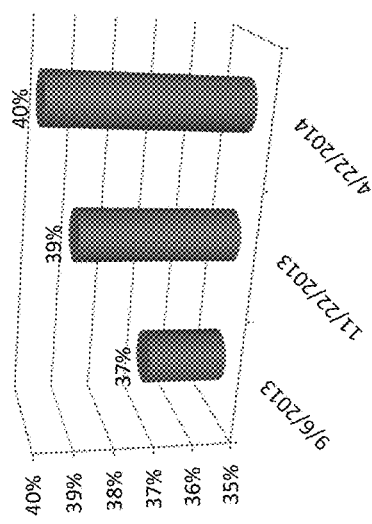
Figure 7J:
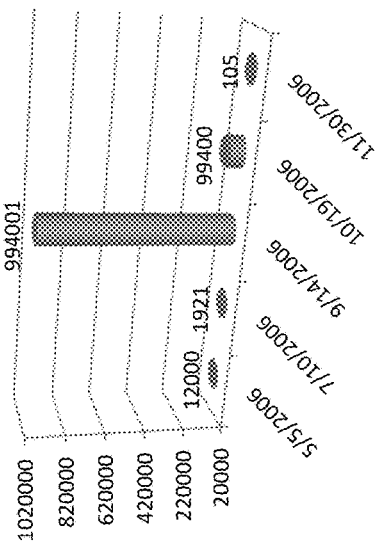

As illustrated in FIGS. 7I-J, the standard treatment appeared to have been effective at suppressing HIV viral counts, as illustrated by the observed reductions in his number of HIV viral copies. As illustrated in FIGS. 7A-H, however, the cellular response to standard therapy appeared to be sluggish and his observed improvements in immunologic cellular parameters such as his absolute CD4+ cell counts, did not achieve or approximate normal lymphocyte concentrations.

Example 8

Figures 8A, 8B:
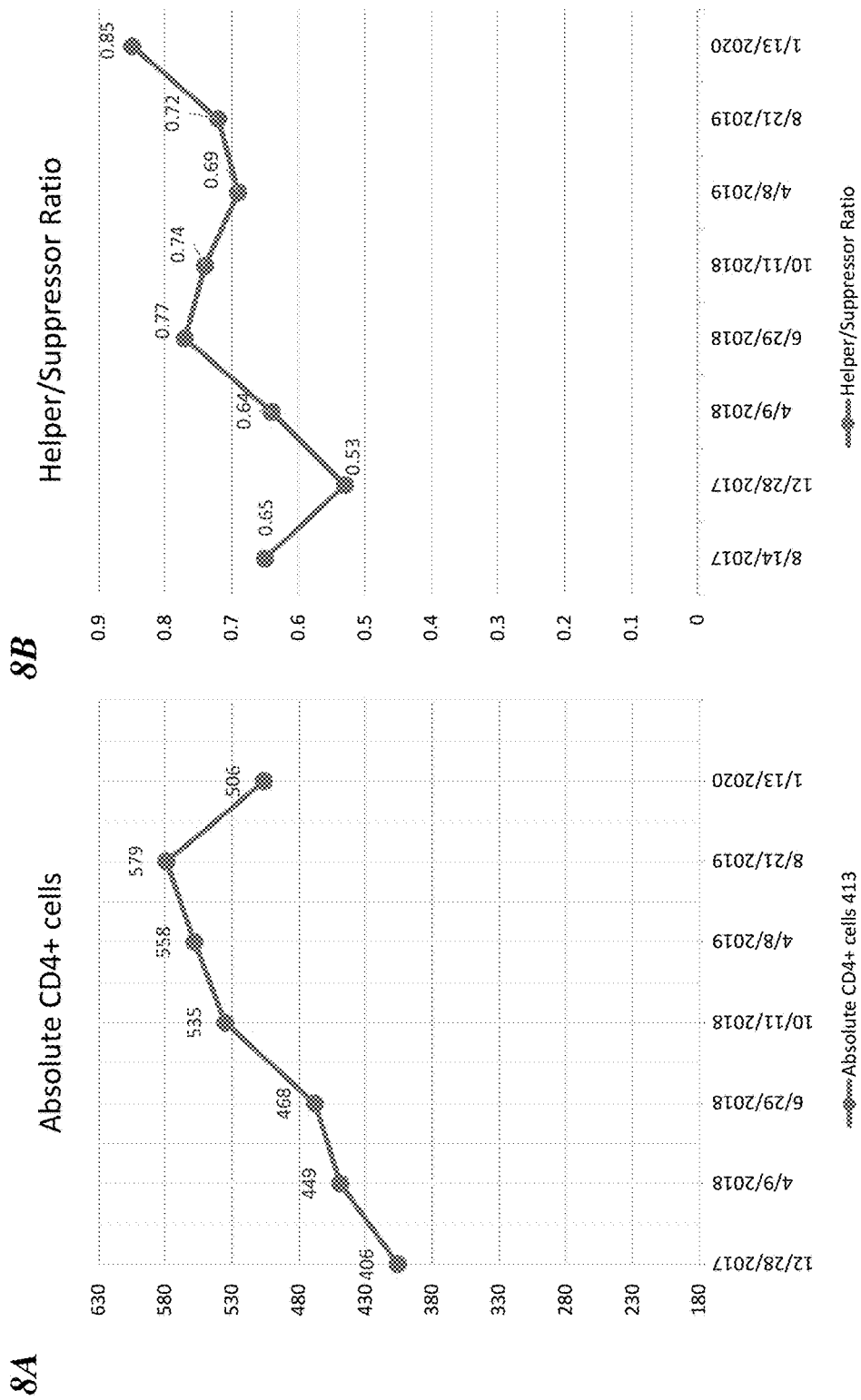
FIGS. 8A-8B illustrate the improvements in immune cellular parameters that were observed in an HIV-positive subject that was administered a combination of a vanadium-containing compound and a sulfonylurea.

SS is a 58-year-old female who has been HIV-positive since 1995, having acquired the disease from her ex-husband who was an intravenous drug user. SS was diagnosed over 23 years ago when her son was born and had the disease prior. She came under the care of the present inventor in August 2017 while receiving adequate antiviral therapy with GENVOYA (elvitegravir, cobicistat, emtricitabine, tenofovir alafenamide), maintaining full HIV viral suppression and consistently undetectable for virus in all her laboratories. Her CD4 cell counts were maintained over 400 cells/μL and were stable, which is often referred to as the plateau phase (see, FIG. 8A). Laboratory abnormalities observed included her immune cell parameters, including an abnormal inverse ratio of CD4/CD8, low CD4% and low absolute CD4, which implied cellular immune decompensation which is typical of HIV infected individuals (see, FIG. 8B). An inverse ratio of CD4/CD8 reflects the presence of HIV pro-viral reservoirs in the nucleus of the immune cells.

In an attempt to purge out the HIV viral reservoirs as much as possible and at the same time destroy as many HIV viruses as possible, SS was prescribed 3 mg glyburide micronized in October 2017 for her to use it together with the 60 mg of vanadyl sulfate. In January 2018, SS reported that she was only taking half of the 3 mg glyburide micronized and was not taking the vanadyl sulfate daily because at times was experiencing symptoms of low glucose levels. As a result of this, her CD4 cell counts diminished as did her CD4/CD8 ratios, while her total lymphocyte counts and CD8 cells increased, implying activation. SS was advised to use only 1.5 mg of micronized glyburide and to use 60 mg of vanadyl sulfate to prevent the hypoglycemic symptoms.

In September 2018, SS revealed that she had only been using the prescribed therapy intermittently due to hypoglycemic symptoms and had discontinued the treatment by the end of September 2018. In November 2018, SS reinitiated the prescribed therapy intermittently and then discontinued it, estimating that she used the advocated therapy for a total amount of 2-3 months.

Despite having discontinue adjunct therapy with vanadyl sulfate and glyburide, the immune competence of SS continued to improve, as reflected by the improved cell parameters and CD4/CD8 ratios. This suggested a profound epigenetic effect, which has restored the innate immune competence of SS, allowing her own immunity to overcome the provirus reservoirs. The present inventor believes that this could potentially result in a cure, as her immunity continues depleting the provirus presence. In particular, since the immune competence of SS, as reflected by improved CD4/CD8 ratios, has continued improving long after discontinuation of the adjunct therapy, this implies an epigenetic reprogramming effect which restores the efficacy of the innate and adaptive immune system against the virus, further depleting provirus reservoirs while restoring immune cell parameters.

Example 9

Figure 9A:
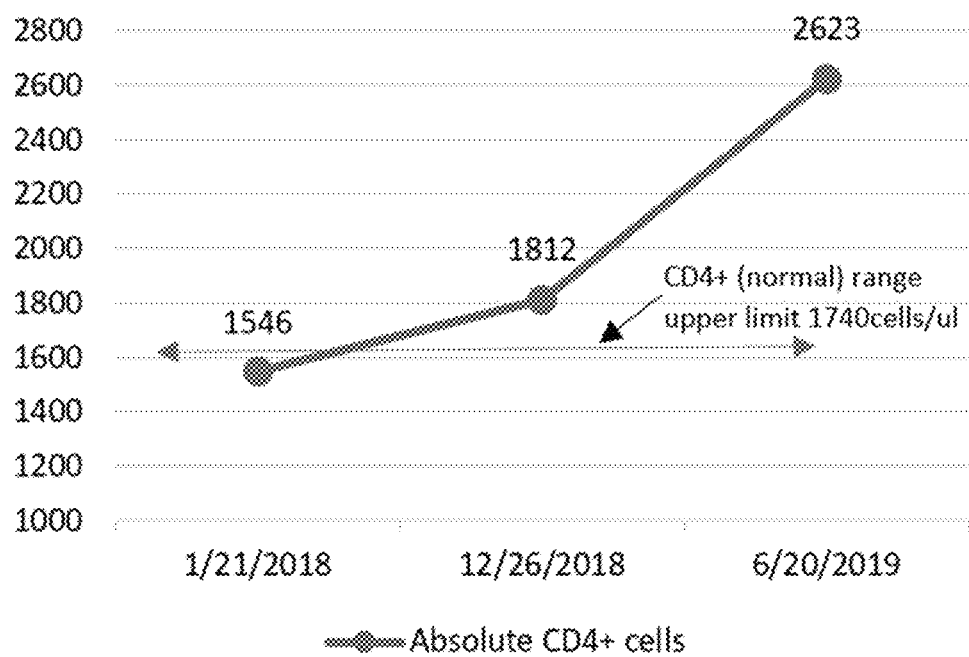
FIGS. 9A-9B illustrate the improvements in immune cellular parameters that were observed in an HIV-positive subject that was administered a combination of a vanadium-containing compound and a sulfonylurea.
Figure 9B:
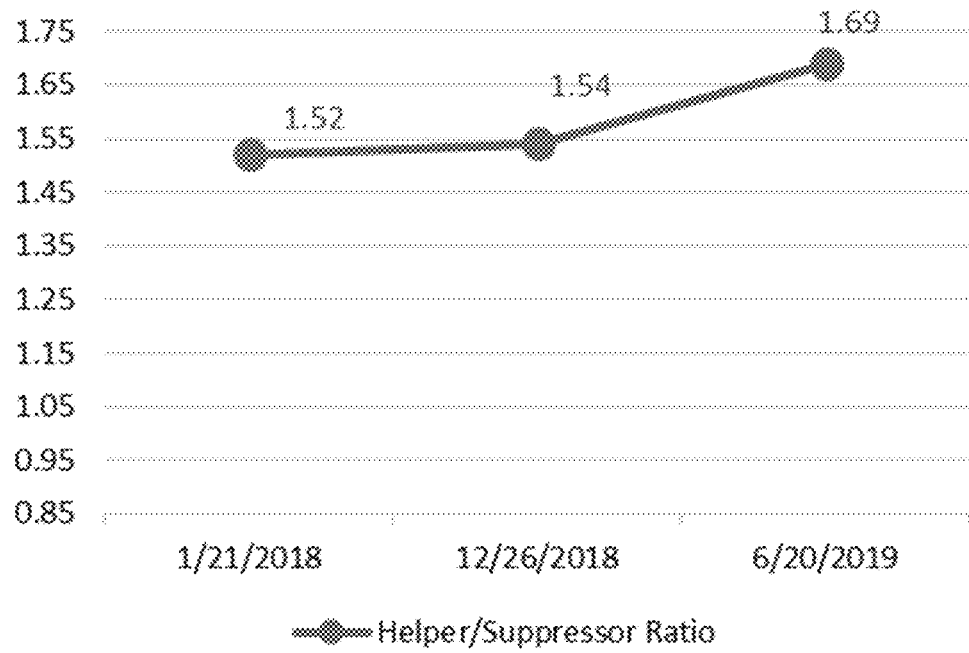

TT is a 39-year-old female who came under the care of the present inventor in March 2017, but only for primary care because her HIV was being managed by a nurse practitioner. TT was being treated for the past six years since diagnosis with ATRIPLA (efavirenz, emtricitabine, tenofovir disoproxil fumarate). According to the consultative reports from the nurse practitioner treating SS, she was stable and her virus was suppressed. As usually occurs, TT was considered HIV-positive, asymptomatic because her CD4 counts were over 200 cells/μL and her virus were being suppressed with ATRIPLA. TT was surprised to learn that her immune cell counts were abnormal, despite having been counseled that she was fine. TT asked whether something could be done about her decompensated cellular immunity and was prescribed adjunct therapy with 60 mg of vanadyl sulfate and 1.5 mg of micronized glyburide, following which a dramatic rise in total lymphocyte counts, including CD8 and CD4 lymphocytes, was observed. The observed increase was well beyond the normal expected cell volume, 50% beyond the maximum normal and the treating nurse practitioner immediately referred TT to an oncologist upon seeing these lab results (FIGS. 9A-9B). Upper limit of normal for CD4 T lymphocyte cells is 1740 cells/μL and 1170 cells/μL for the CD8 T lymphocytes.

The observed increases in immune cell volume was not cancer, but only the result of exposing the hidden virus to TT's immune system, which resulted in a dramatic cellular response and would likely level due to depletion of infected clones. Based on the foregoing observations, it is believed that adjunct therapy with vanadyl sulfate and glyburide exposed the hidden provirus reservoirs to the subject's immune system, which then caused a vigorous immune response.

Example 10

JJ is a 63-year-old female who came under the care of the present inventor in August 2016, was a former intravenous drug user and reported having HIV for 25 years. JJ has never used antiviral therapy for the treatment of her HIV and refuses to use any conventional antiviral therapies because she has natural resistance and very mild disease with virus counts usually under 100, and very seldom slightly over 100 viruses per deciliter. This condition is often referred to as an elite controller.

Figure 10A:
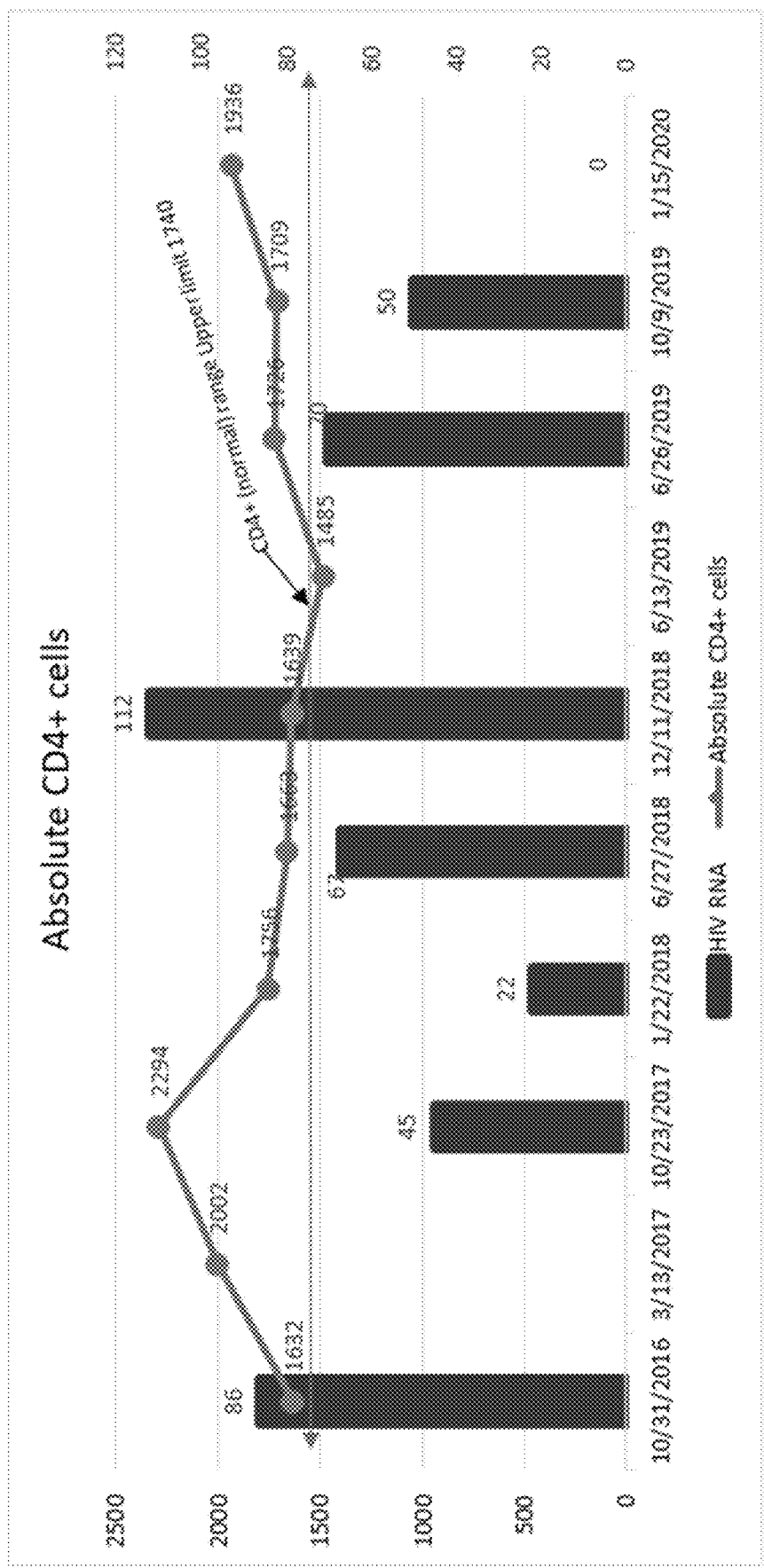
FIGS. 10A-10C illustrate the improvements in immune cellular parameters that were observed in an HIV-positive subject that was administered a combination of a vanadium-containing compound and a sulfonylurea.
Figure 10B:
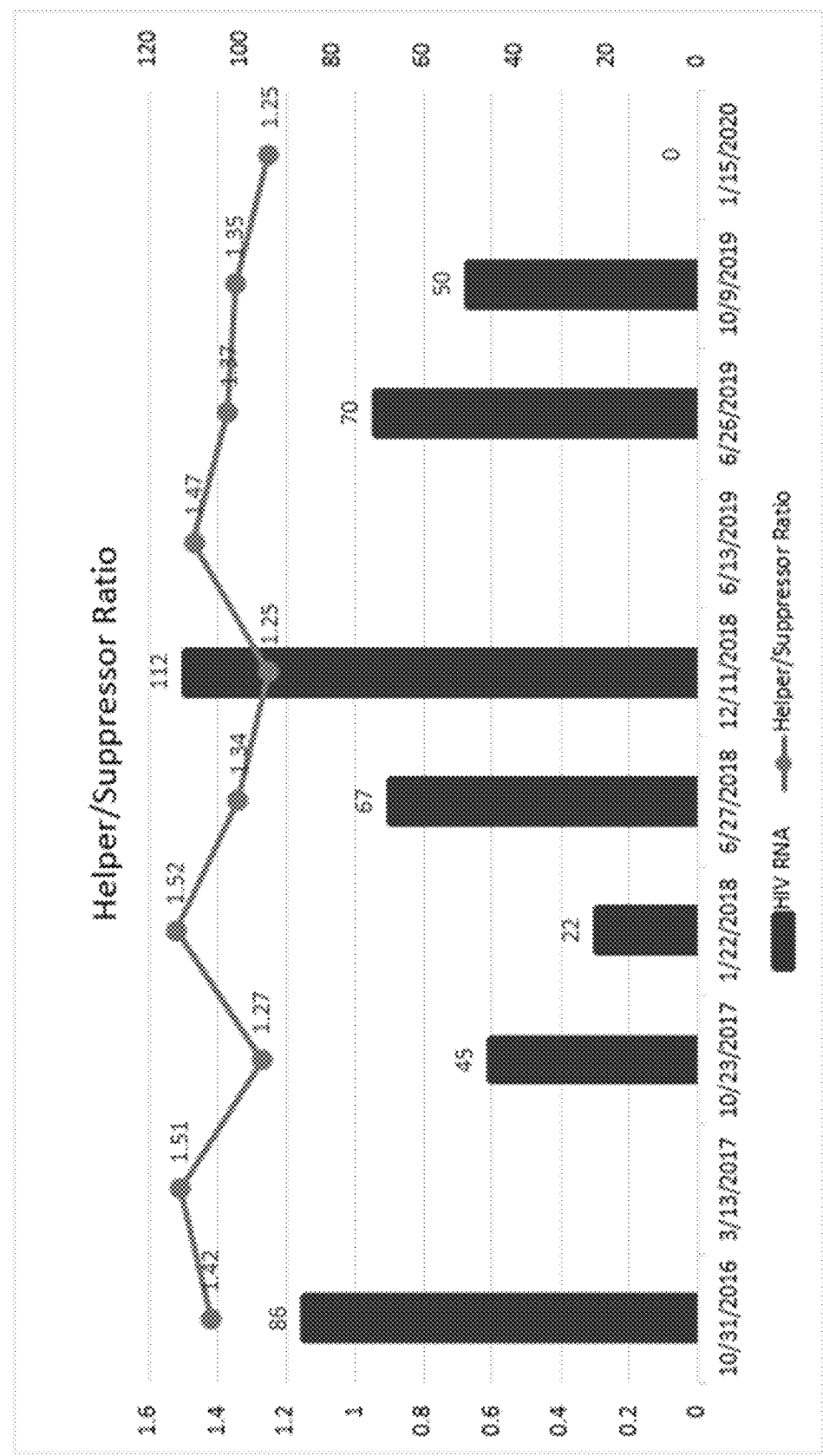
Figure 10C:
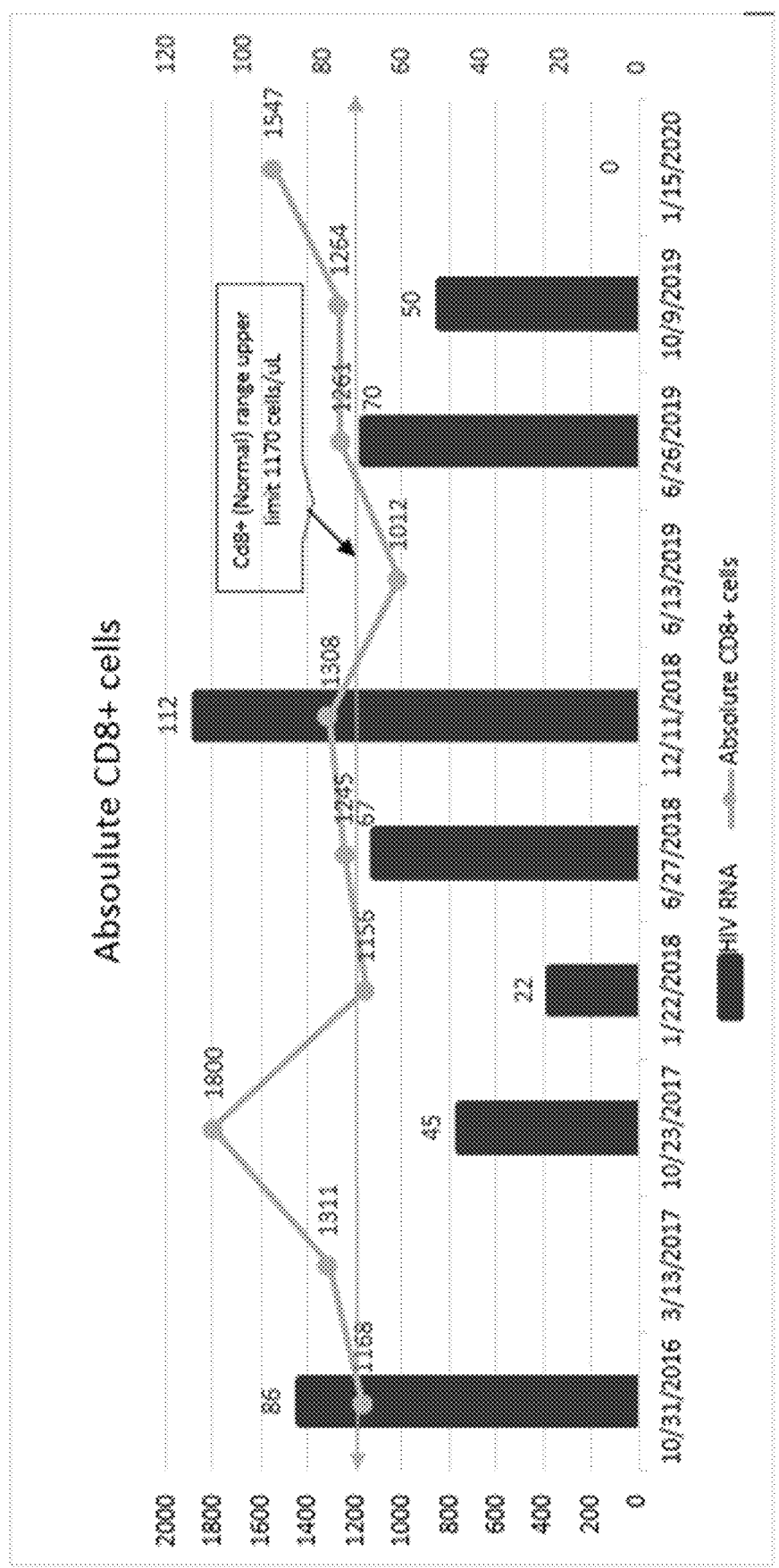

Upon reviewing JJ's laboratories, she always has some virus detectable and her immune cells (lymphocytes) appeared to remain in an activated state based on her elevated CD8 lymphocyte count, often over the upper limit of normal. Upper limit of normal for CD4 T lymphocyte cells is 1740 cells/μL (FIG. 10A) and 1170 cells/μL for the CD8 T lymphocytes (FIG. 10B). In May 2017, JJ was prescribed for the first time 3 mg of micronized glyburide with 60 mg of vanadyl sulfate for the purpose of attempting to purge out any residual HIV virus in her body. After approximately 30 months of treatment and an enhanced activated state as a result of the prescribed therapy, for the first time the HIV virus has become undetectable (FIGS.

10A-10C). This implied that the prescribed therapy had direct antiviral properties, in addition to the antiviral properties typically observed when such therapy is used as adjunct therapy in conjunction with antivirals.

Based on the foregoing results, it is believed that the advocated therapy of micronized glyburide and vanadyl sulfate had indirect anti-HIV provirus properties which operate via activation of the immune system, then permitting the innate and adaptive immune system to overcome the provirus reservoirs. In this case the viral presence became undetectable for the first time after a prolonged period of treatment using only vanadyl sulfate and micronized glyburide, and despite this patient having never used conventional antiviral treatment.

Example 11

VW is a 45-year-old patient that came under the care of the present inventor in June 2017, presenting with morbid obesity and HIV-positive. She was in preparation for bariatric surgery. Her HIV was being treated with TRIUMEQ (abacavir, dolutegravir, lamivudine). In October 2017, VW underwent bariatric surgery and in April 2018, the patient revealed for the first time that she had not been taking the prescribed antiviral therapy or the adjunct vanadyl sulfate and micronized glyburide combination due to extreme difficulty swallowing pills or any solids post-surgery and non-understanding what the vanadyl sulfate and glyburide were being used for.

Figure 11A:
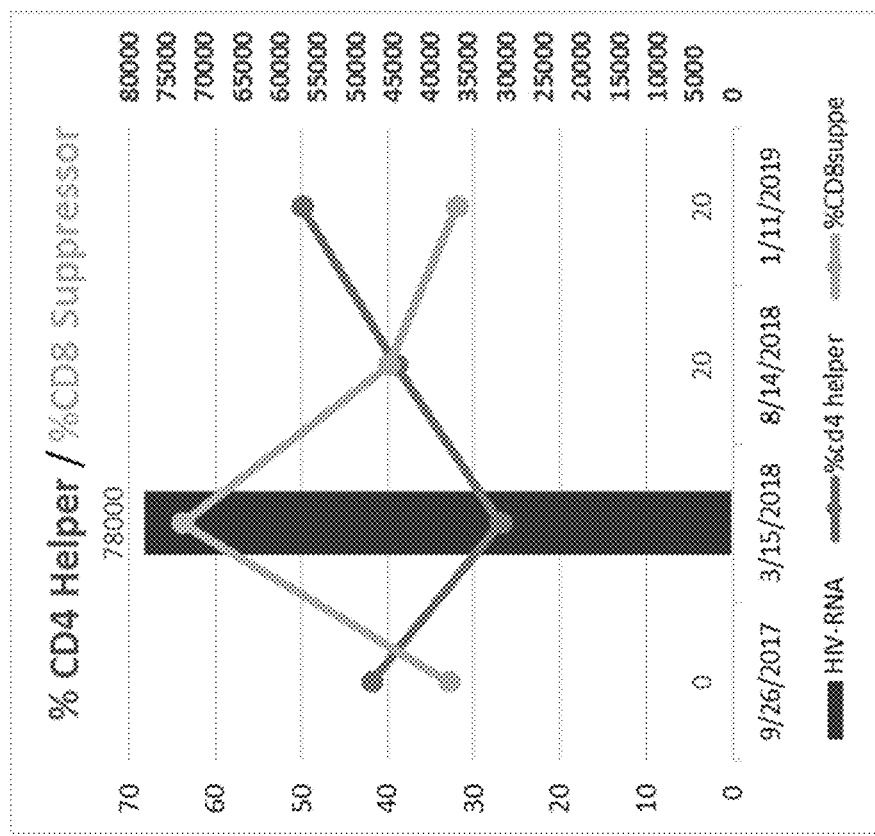
FIGS. 11A-11F illustrate the improvement in various cell lines that were observed in an HIV-positive subject that was administered a combination of a vanadium-containing compound and a sulfonylurea.
Figure 11B:
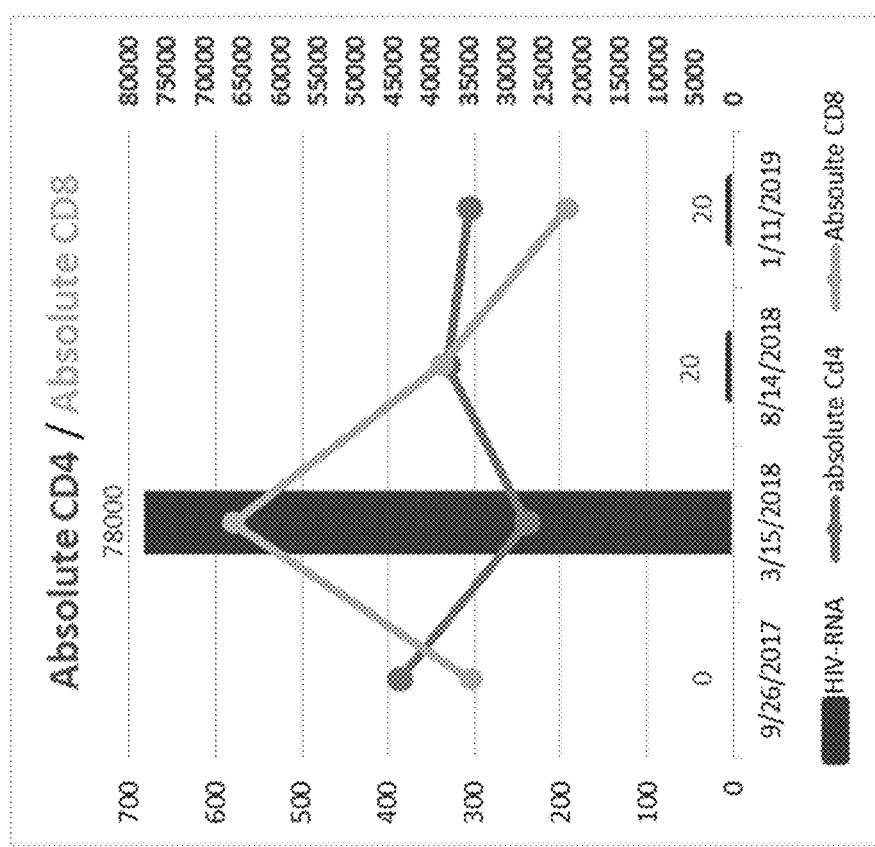
Figure 11C:
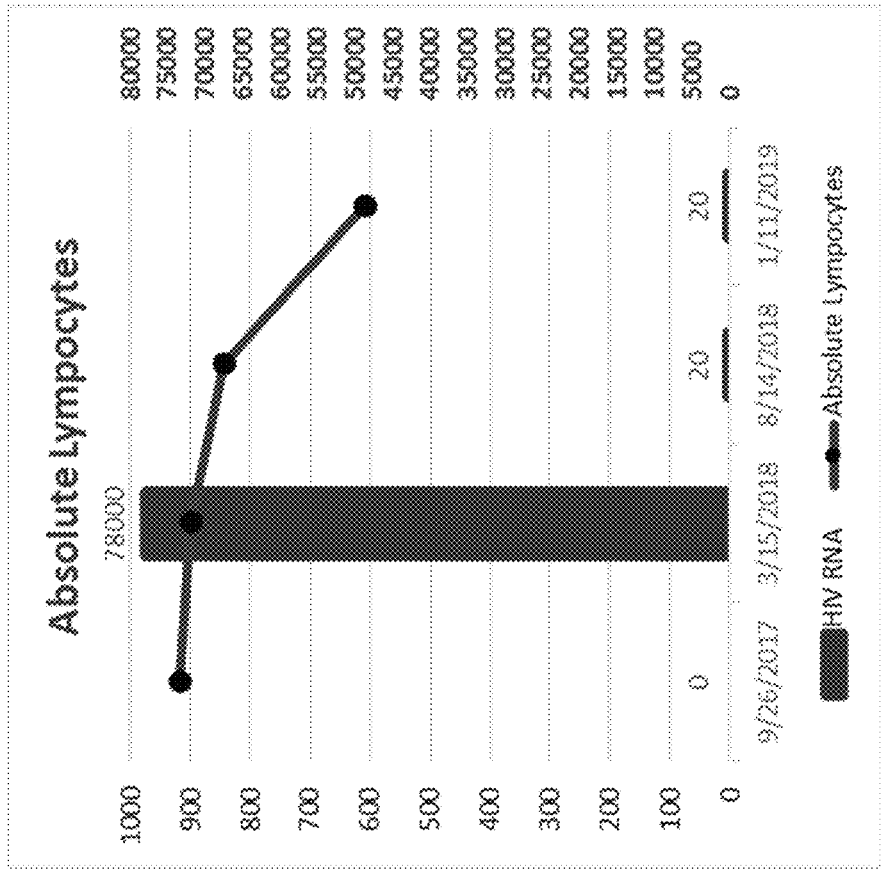
Figure 11D:
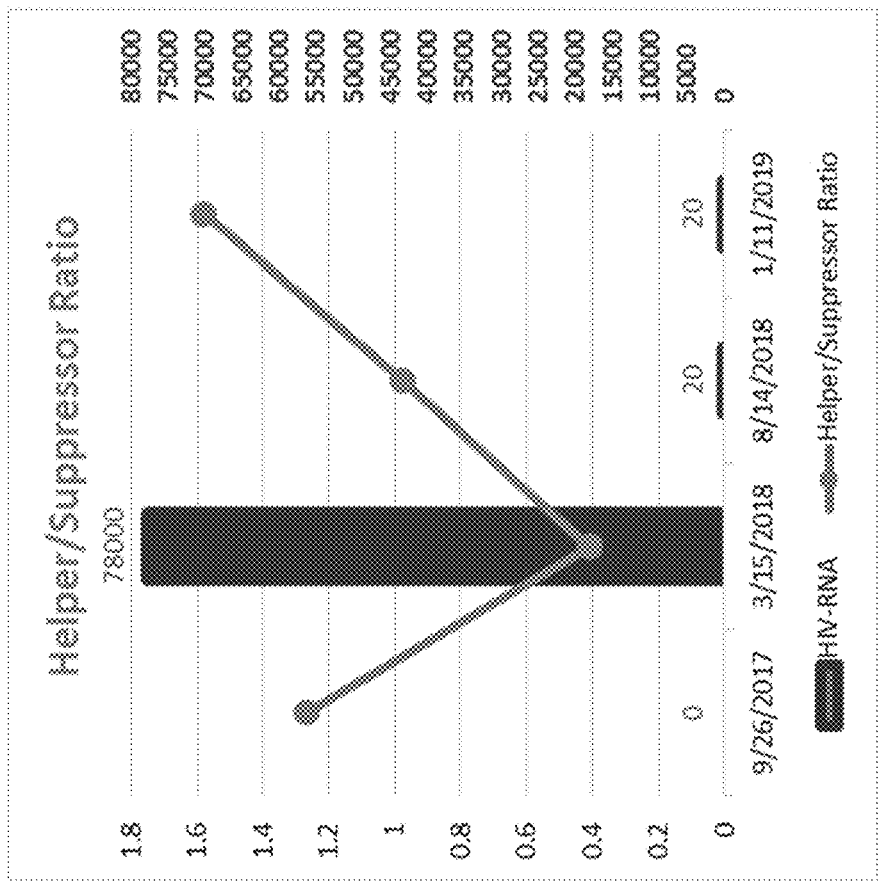
Figure 11E:
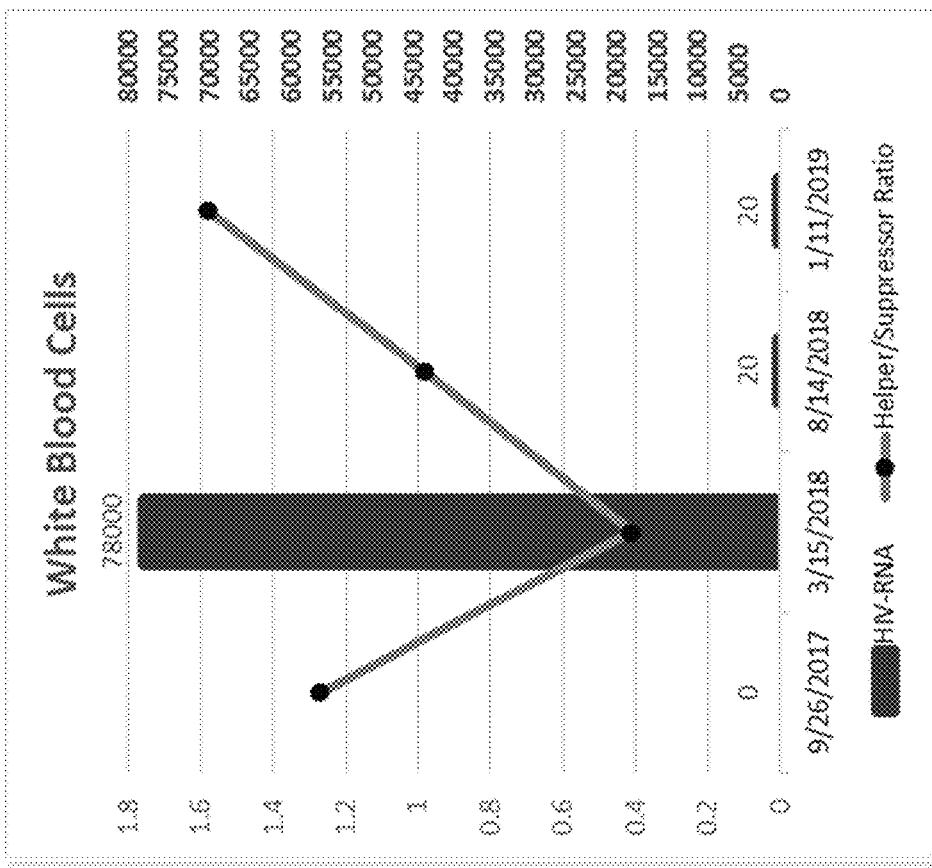
Figure 11F:
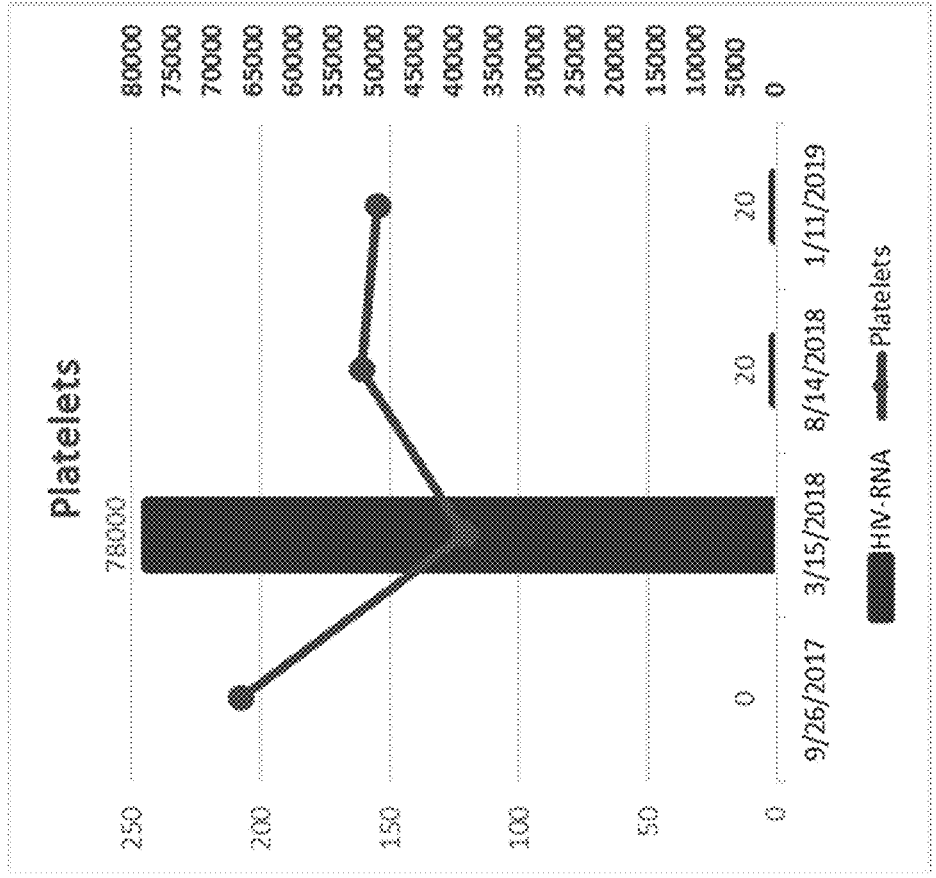

VW re-initiated treatment in April 2018 with BIKTARVY (bictegravir, emtricitabine, tenofovir alafenamide) because the size of the tablet was smaller and easier to swallow. The advocated therapy of 60 mg of vanadyl sulfate and 1.5 mg of micronized glyburide micronized was added as an adjunct treatment. A dramatic improvement in CD4 T lymphocyte counts and CD4/CD8 ratios and reduction in total lymphocyte counts and CD8% were observed, suggesting deactivation and clearance of the HIV virus and reduction of provirus reservoir (FIGS. 11A-11C). Because provirus volume in the nucleus is so difficult to measure it has become widely accepted that the observed improvements in lymphocyte ratios and delayed virus rebound are a reflection of reduced provirus volume. Surprisingly other cell lines from the hematopoietic system also improved simultaneously and concordantly, such as platelets and white blood cells (FIGS. 11E-11F), suggesting restoration of the hematopoietic system and the recovery of CD34 hematopoietic stem cell function. The observed rise and recovery of various cell lines including platelets, neutrophils, monocytes, erythrocytes are commonly observed in these patients when treated in this fashion and suggests a reduction or disruption of HIV provirus reservoir in the bone marrow CD34+ progenitor hemopoietic stem cells. The foregoing observations suggest that the advocated treatment restores the hemopoietic stem cells, resulting in recovery of adequate volume of various cell lines derived from multipotential bone marrow stem cells.

Example 12

Figures 12A, 12B:
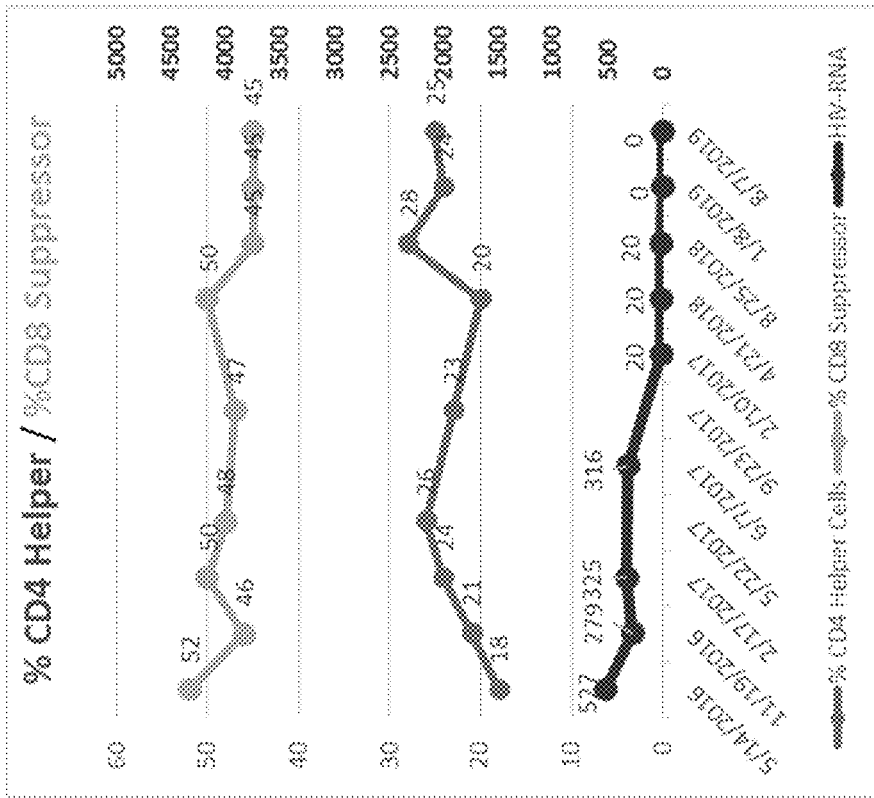
FIGS. 12A-12F illustrate the improvement in various cell lines that were observed in an HIV-positive subject that was administered a combination of a vanadium-containing compound and a sulfonylurea.
Figures 12C, 12D:
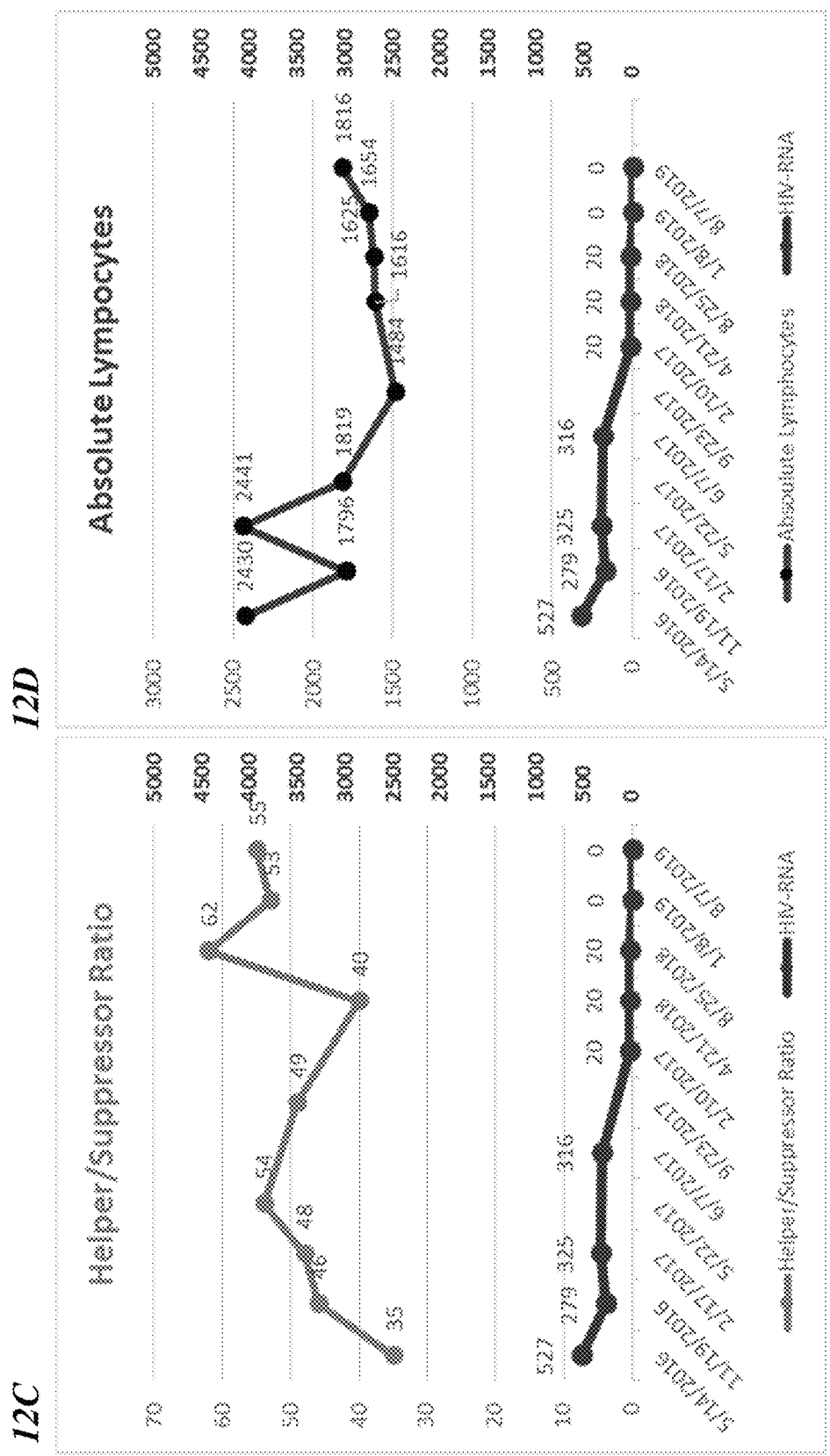
Figures 12E, 12F:
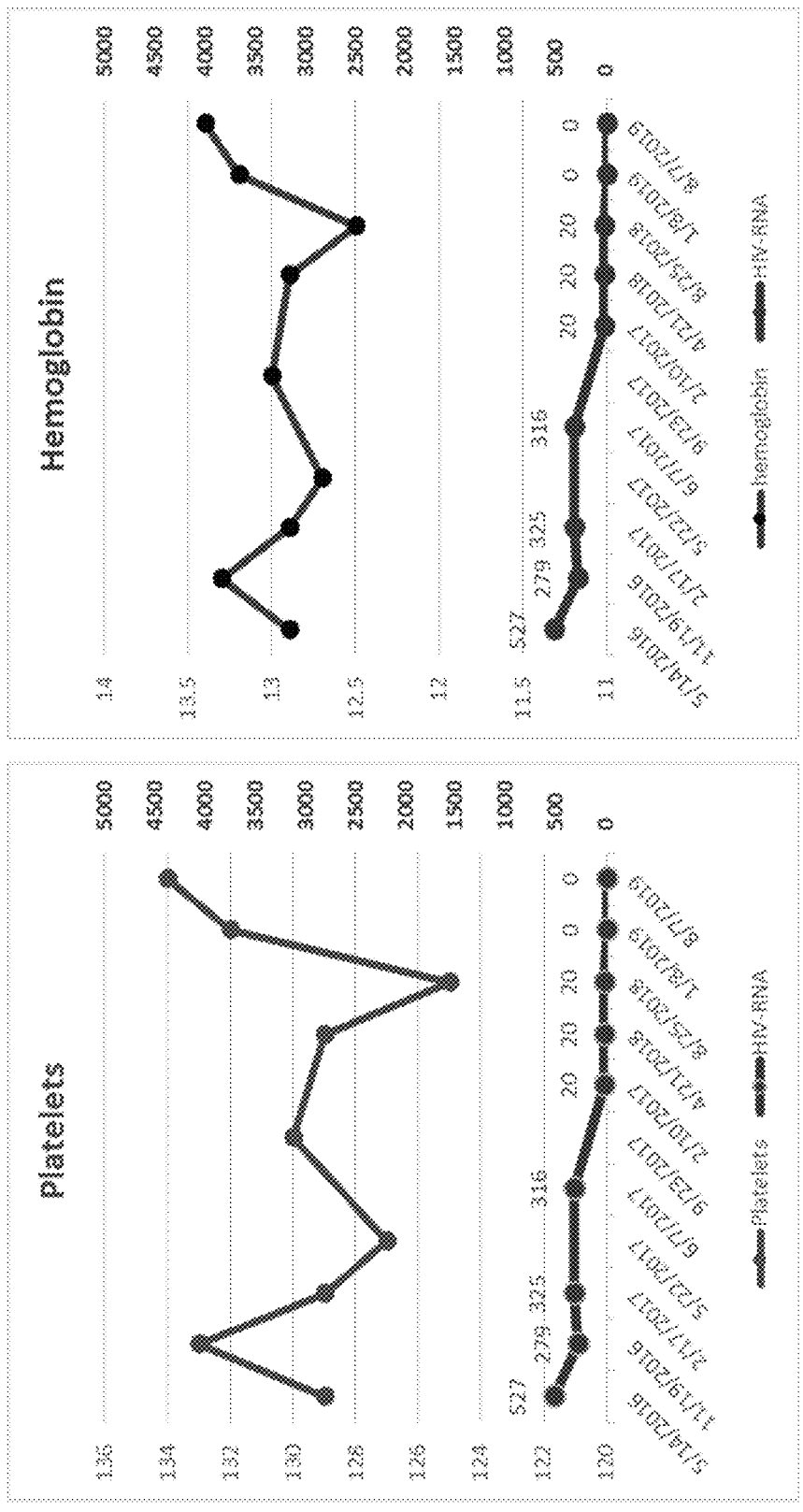

FC is a 57-year-old male that came under the care of the present inventor in October 2016, having been HIV-positive since 2003 and prescribed PREZISTA (darunavir), NORVIR (ritonavir) and EPZICOM (abacavir, lamivudine). FC has a history of antiviral resistance and, in spite of receiving potent and effective antiviral therapies, including protease inhibitors, he always had some detectable virus and could never achieve complete virus suppression to undetectability. In May 2017 FC was started on GENVOYA (elvitegravir, cobicistat, emtricitabine, tenofovir alafenamide) and continued to maintain detectable viral presence. In November 2016, FC was prescribed and began taking adjunct therapy of vanadyl sulfate and glyburide. In January 2019, FC became virally undetectable (FIGS. 12A-12F) and reported feeling stronger and lighter, as if a weight had been lifted off of his body. Notably, when FC's CD4/CD8 ratio improved, so did the hemoglobin and also the platelets and simultaneously the detectable virus disappeared (FIGS. 12E-12F). Based on the foregoing observations, the advocated therapy improves multiple bone marrow derived cell lines, while also leading to the recovery of the immune cell parameters and reducing provirus reservoirs.

Example 13

Figure 13:
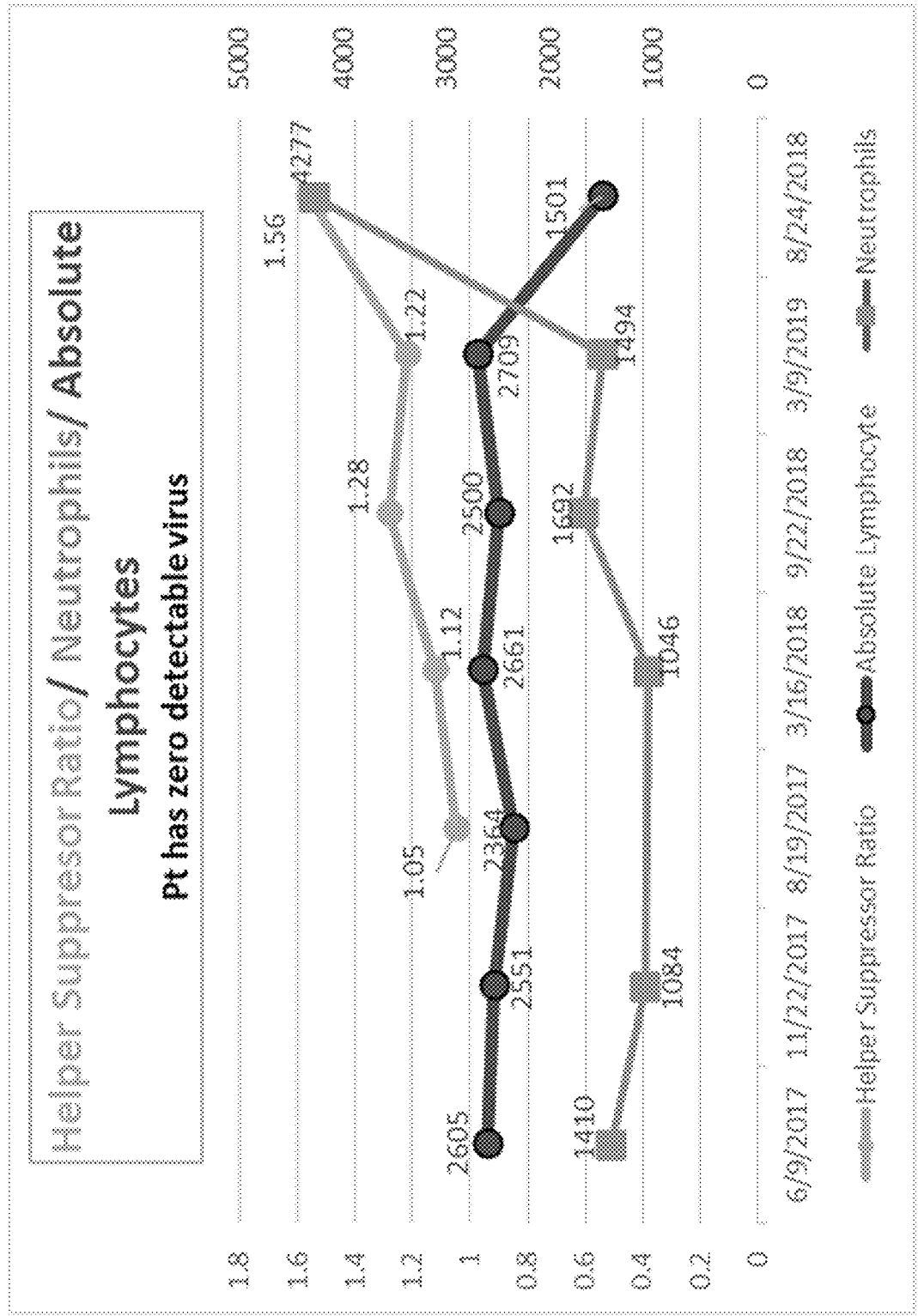
FIG. 13 depicts the effects on various cell lines that were observed in an HIV-positive subject that was administered a combination of a vanadium-containing compound and a sulfonylurea.

EA presented with low neutrophil counts and no detectable virus, and treatment was initiated in January 2018 with 60 mg of vanadyl sulfate and 1.5 mg micronized glyburide daily, but was discontinued due to adverse effects and subsequently resumed in March 2018. As illustrated in FIG. 13, a result of the treatment with vanadyl sulfate and micronized glyburide, EA's neutrophil counts increased considerably and was accompanied by a concomitant increase in the CD4/CD8 ratio. The absolute lymphocyte counts decreased probably due to lymphocyte deactivation and depletion of HIV virus reservoirs.

Example 14

CV is a male HIV-positive patient who came under the care of the present inventor in 2015 while receiving ATRIPLA (efavirenz, emtricitabine, tenofovir). CV had been HIV-positive for 20 years and was very concerned about developing leukemia because he always had low leukocyte counts. CV was prescribed vanadyl sulfate 60 mg and 3 mg of micronized glyburide, following which an improvement in leukocytes and neutrophil counts were observed.

Figure 14:
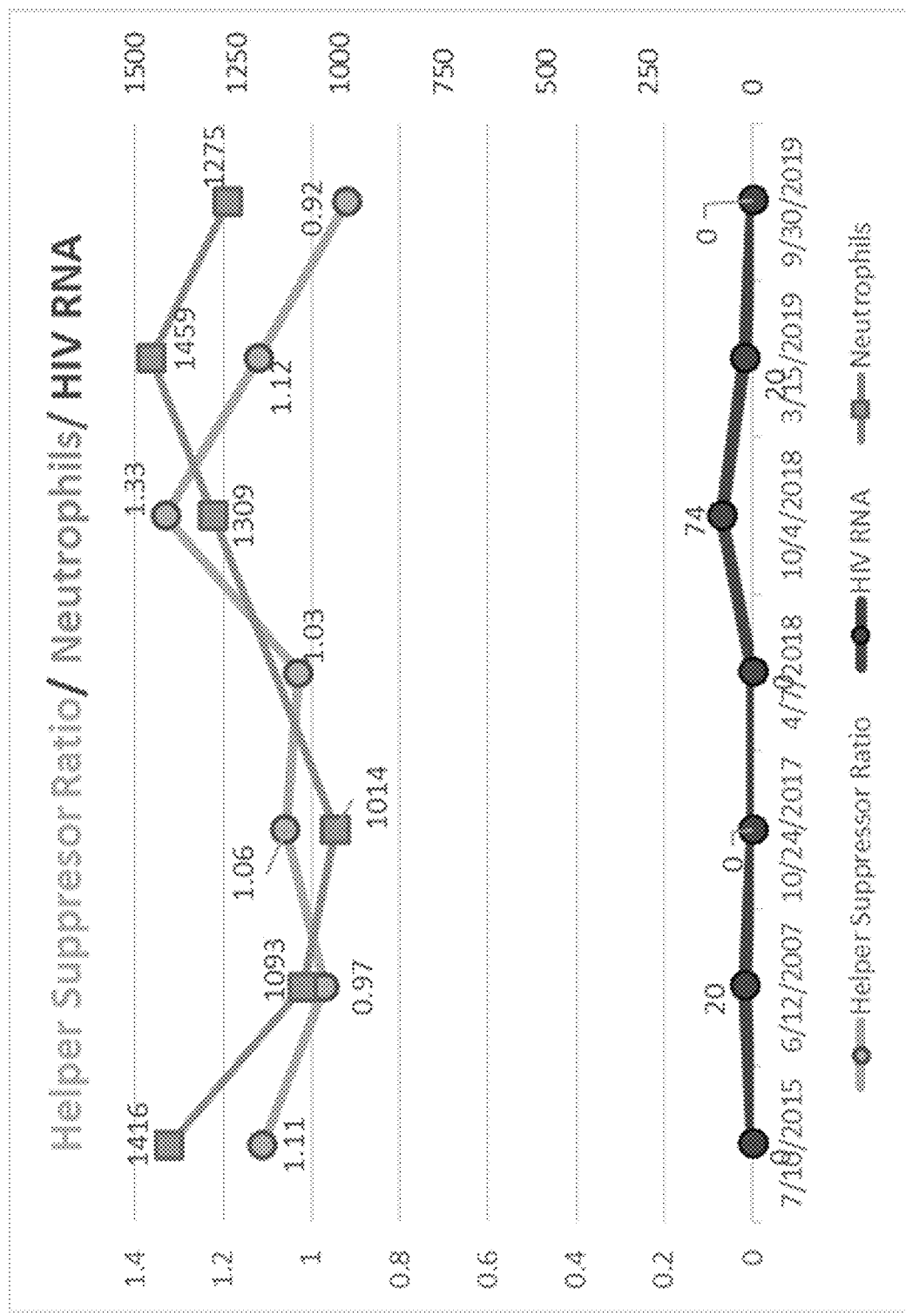
FIG. 14 depicts the effects on various cell lines and viral load that were observed in an HIV-positive subject that was administered a combination of a vanadium-containing compound and a sulfonylurea.

During 2016 and 2017, CV was seeing several different hematologists and out of frustration due to not having been offered effective treatment, treatment with vanadyl sulfate and micronized glyburide was reinitiated and, as depicted in FIG. 14, improvements in CV's neutrophil counts and CD4/CD8 cell ratio were observed between 2017 and 2019. The subsequently observed reductions were believed to be due to changing antiretroviral therapy from ATRIPLA to DELSTRIGO (doravirine, lamivudine, tenofovir disoproxil fumarate) during the second half of 2019.

Example 15

RR is a 41-year-old female who developed estrogen sensitive moderately differentiated ductal breast carcinoma in 2011. She was initially treated with neoadjuvant systemic chemotherapy AC (doxorubicin and cyclophosphamide) followed by TAXOL (paclitaxel) followed by modified radical mastectomy. She then received post-operative external radiation for T4dN2aMO, Stage IIIB. In April 2012, RR's PET scan showed moderate progression with metastatic disease to the bone and liver. She then received palliative radiation to C6-T3 and was changed from tamoxifen to AROMASIN (exemestane) 20 mg daily on May 2012. The PET scan in December 2012 showed progression of disease with liver and bone involvement so RR was changed to XELODA (capecitabine) in December 2012 for three cycles, then changed to AFFINITOR (everolimus) with AROMASIN. In March 2014 she manifested worsening of disease with liver and bone metastasis.

The patient was seen by the present inventor stating she had received multiple chemo cycles without improvements and she was led to believe there was nothing more which could be offered to her. RR was prescribed 1.5 mg micronized glyburide and 60 mg of vanadyl sulfate and the next PET scan in August 2013 showed no evidence of cancer. She had also changed her chemotherapeutic regimen from a combination of AFFINITOR and AROMASIN from XELODA. The patient explained that the prescribed treatment had cleared the bone metastasis and the liver metastasis was shrinking so for the reason the oncologist switched her treatment to AFFINITOR which, like vanadium, is a tyrosine phosphokinase inhibitor. RR took the prescribed therapy for 2-3 months and at the end of 2019 she developed brain metastasis for which she was receiving radiation and steroid, however she expired shortly after. During the brief time that RR took the vanadyl sulfate and glyburide she had significant improvement which was not sustained with the AFFINITOR. The glyburide alone she continued using due to hyperglycemia produced by the steroids given her. This case further exemplifies the efficacy of the inventions disclosed herein. Vanadium, with enhanced cellular penetration resulting from the co-administered sulfonylurea, achieved a dramatic positive response in an advanced metastatic breast cancer patient.

Example 16

LT is a 63-year-old male initially seen by the present inventor and immediately sent to the ER on Dec. 29, 2016, were he received 4 pints of blood for a hgb of 5 g/dl. He was diagnosed myelodysplastic syndrome with ring sideroblast (RARS) with abnormal cytogenetics 45, X, Y+8(20) male karyotype. The patient was advised to consider and initiate the process for Allo-HSCT bone marrow stem cell transplant. LT elected to not consider this treatment option and placed a hold on this decision. He was instead started on PROCRIT (epoetin alfa) 40,000 units weekly and subsequently increased to 60,000 units. It is known that erythropoietin would be ineffective for this condition per published medical scientific literature. LT received PROCRIT and the advocated therapy of vanadyl sulfate and micronized glyburide for approximately four months and his hemoglobin remained relatively stable at around 7%. This improvement and stabilization were discussed with LT and he acknowledged it. Since he was going to start a new chemotherapeutic regimen, he was instructed to discontinue the advocated treatment of vanadyl and glyburide. LT was started on VIDAZA (azacitidine) in August 2017, for several cycles. Upon initiating the chemotherapy LT was instructed to discontinue the vanadyl sulfate and glyburide combination to see if would respond to the chemo. He was having considerable adverse side effects to the chemo and one month later developed pneumonia and expired. The present inventor believes that the patient benefited from this treatment because his hemoglobin remained stable for several months at or near 7 G/dl. It appears the advocated treatment has cellular growth factor like effects in myelodysplastic syndromes implying a nuclear mechanism of action.

DISCUSSION

The present inventor has determined that it is possible to insert a potent antiviral into the intracellular compartment which is capable of killing the virus and the provirions and block further viral cell penetration. This, when achieved, resulted in increased CD4 cell count and normalization of the CD4/CD8 cell ratios.

Without wishing to be bound by any particular theory, it is believed that the potassium channel provides a method of achieving a doorway penetration into the intracellular compartment in the human mammalian cell by using vanadium, a sulfonylurea 2 (SUR2) agonist, and micronized glyburide, a potent sulfonylurea 1 (SUR 1) agonist. It is believed that the intracellular introduction of the virucidal vanadium complex kills the virus and further blocks entry via the CCR5 receptor, thereby achieving cures. Direct viral killing by vanadium and disruption of provirions genomic attachment and replication indicates that this method could be a potential cure to viral or retroviral infectious diseases, such as HIV. Manipulation of the sulfonylurea receptors in the potassium channels plays a critical role in vanadium penetration and biological action in human mammalian cells.

The improvement in immune function demonstrated in the foregoing Examples are surprising and unexpected, at least because the CD4 T lymphocyte counts increase significantly and the CD4/CD8 lymphocyte ratios improved dramatically. These surprising and unexpected observations suggest reductions in immune activation in view of reduced CD5 counts and increase in CD4 counts and further suggest reductions in viral reservoir and disease burden leading to immune reconstitution and restoration.

What is claimed is:

1. A method of reconstituting the immune system of a subject in need thereof and having human immunodeficiency virus (HIV) or acquired immunodeficiency syndrome (AIDS) by improving one or more of CD4 counts and CD4/CD8 lymphocyte cell ratios in the subject, the method comprising administering to the subject an effective amount of vanadyl sulfate and an effective amount of glyburide, thereby improving one or more of the CD4 counts and CD4/CD8 lymphocyte cell ratios in the subject.

2. The method of claim 1, wherein an effective amount of the vanadyl sulfate is from about 60 mg to about 120 mg per day.

3. The method of claim 1, wherein an effective amount of the glyburide is from about 0.75 mg to about 12 mg per day.

4. The method of claim 1, wherein the glyburide is micronized.

5. The method of claim 1, further comprising administering one or more antiviral or antiretroviral compounds to the subject.

6. The method of claim 1, wherein the method further reduces the subject's viral load.

7. A method of increasing CD4 counts in a subject in need thereof and having human immunodeficiency virus (HIV) or acquired immunodeficiency syndrome (AIDS), the method comprising administering to the subject an effective amount of vanadyl sulfate and an effective amount of glyburide, thereby increasing the CD4 counts in the subject.

8. The method of claim 7, wherein an effective amount of the vanadyl sulfate is from about 60 mg to about 120 mg per day.

9. The method of claim 7, wherein an effective amount of the glyburide is from about 0.75 mg to about 12 mg per day.

10. The method of claim 7, wherein the glyburide is micronized.

11. The method of claim 7, further comprising administering one or more antiviral or antiretroviral compounds to the subject.

12. The method of claim 7, wherein the method further reduces the subject's viral load.

13. A method of improving CD4/CD8 lymphocyte cell ratios in the subject in need thereof and having human immunodeficiency virus (HIV) or acquired immunodeficiency syndrome (AIDS), the method comprising administering to the subject an effective amount of vanadyl sulfate and an effective amount of glyburide, thereby improving CD4/CD8 lymphocyte cell ratios in the subject.

14. The method of claim 13, wherein an effective amount of the vanadyl sulfate is from about 60 mg to about 120 mg per day.

15. The method of claim 13, wherein an effective amount of the glyburide is from about 0.75 mg to about 12 mg per day.

16. The method of claim 13, wherein the glyburide is micronized.

17. The method of claim 13, further comprising administering one or more antiviral or antiretroviral compounds to the subject.

18. The method of claim 13, wherein the method further reduces the subject's viral load.

\* \* \* \* \*